(12) United States Patent  
Kimura et al.

(10) Patent No.: US 10,059,817 B2
(45) Date of Patent: Aug. 28, 2018

(54) METHOD FOR PRODUCING POLYACRYLIC ACID (SALT)-BASED WATER ABSORBING AGENT, AND WATER ABSORBING AGENT

(71) Applicant: NIPPON SHOKUBAI CO., LTD., Osaka-shi, Osaka (JP)

(72) Inventors: Kazuki Kimura, Himeji (JP); Yusuke Watanabe, Himeji (JP); Sayaka Machida, Himeji (JP); Taku Fujimoto, Himeji (JP); Kenji Kadonaga, Himeji (JP)

(73) Assignee: NIPPON SHOKUBAI CO., LTD., Osaka-shi, Osaka (JP)

( * ) Notice: Subject to any disclaimer, the term of this patent is extended or adjusted under 35 U.S.C. 154(b) by 0 days.

(21) Appl. No.: 15/297,322

(22) Filed: Oct. 19, 2016

(65) Prior Publication Data

US 2017/0044332 A1 Feb. 16, 2017

Related U.S. Application Data

(62) Division of application No. 14/426,539, filed as application No. PCT/JP2013/072207 on Aug. 20, 2013, now Pat. No. 9,518,180.

(30) Foreign Application Priority Data

Sep. 11, 2012 (JP) .................. 2012-199923

(51) Int. Cl.
| | |
|---|---|
| *C08J 3/24* | (2006.01) |
| *A61L 15/24* | (2006.01) |
| *A61L 15/60* | (2006.01) |
| *B01J 20/26* | (2006.01) |
| *C08F 220/06* | (2006.01) |
| *C08L 33/02* | (2006.01) |

(52) U.S. Cl.
CPC .............. *C08J 3/245* (2013.01); *A61L 15/24* (2013.01); *A61L 15/60* (2013.01); *B01J 20/267* (2013.01); *C08F 220/06* (2013.01); *C08L 33/02* (2013.01); *C08J 2333/02* (2013.01); *C08L 2203/02* (2013.01)

(58) Field of Classification Search
CPC ....... A61L 15/60; B01J 20/267; C08F 220/06; C08J 3/24; C08J 3/245; C08J 2333/02; C08L 33/02; C08L 2203/02
USPC ............................... 525/329.1, 187
See application file for complete search history.

(56) References Cited

U.S. PATENT DOCUMENTS

| | | |
|---|---|---|
| 4,734,478 A | 3/1988 | Tsubakimoto |
| 4,755,562 A | 7/1988 | Alexander |
| 4,783,510 A | 11/1988 | Saotome |
| 4,824,901 A | 4/1989 | Alexander |
| 4,920,202 A | 4/1990 | Irie |
| 5,409,771 A | 4/1995 | Dahmen |
| 5,610,208 A | 3/1997 | Dairoku |
| 5,669,894 A | 9/1997 | Goldman et al. |
| 5,672,633 A | 9/1997 | Brehm |
| 6,239,230 B1 | 5/2001 | Eckert |
| 6,265,488 B1 | 7/2001 | Fujino |
| 6,297,319 B1 | 10/2001 | Nagasuna |
| 6,297,335 B1 | 10/2001 | Funk |
| 6,372,852 B2 | 4/2002 | Hitomi |
| 6,472,478 B1 | 10/2002 | Funk |
| 6,559,239 B1 | 5/2003 | Riegel |
| 6,605,673 B1 | 8/2003 | Mertens |
| 6,620,889 B1 | 9/2003 | Mertens et al. |
| 6,657,015 B1 | 12/2003 | Riegel |
| 6,809,158 B2 | 10/2004 | Ikeuchi |
| 7,098,284 B2 | 8/2006 | Torii et al. |
| 7,201,941 B2 | 4/2007 | Irie |
| 7,473,739 B2 | 1/2009 | Dairoku et al. |
| 2002/0061978 A1 | 5/2002 | Hatsuda |
| 2003/0207997 A1 | 11/2003 | Mertens |
| 2004/0071966 A1 | 4/2004 | Inger |
| 2004/0176544 A1 | 9/2004 | Mertens |
| 2004/0176557 A1 | 9/2004 | Mertens |
| 2004/0186244 A1 | 9/2004 | Hatsuda |
| 2005/0020780 A1 | 1/2005 | Inger |
| 2006/0204755 A1 | 9/2006 | Torii et al. |
| 2007/0129495 A1 | 6/2007 | Mertens |
| 2007/0161759 A1 | 7/2007 | Riegel |
| 2008/0021131 A1 | 1/2008 | Mertens |

(Continued)

FOREIGN PATENT DOCUMENTS

| | | |
|---|---|---|
| CN | 102482433 A | 5/2012 |
| CN | 102574100 A | 7/2012 |

(Continued)

OTHER PUBLICATIONS

English translation of International Preliminary Report on Patentability (Chapter 1) of PCT/JP2013/072207 dated Mar. 26, 2015.

(Continued)

*Primary Examiner* — Wenwen Cai
(74) *Attorney, Agent, or Firm* — Dickinson Wright PLLC

(57) ABSTRACT

The present invention relates to an absorbent suitable for use in a thin sanitary material/absorbent article having a high absorbent content and not prone to gel blocking, the absorbent having excellent liquid diffusibility (e.g. SFC) and minimal decrease in absorption ratio under pressure (e.g., AAP or PUP) even when a liquid permeation enhancer is added, and to a method for manufacturing the high-performance absorbent stably during actual production. The method is a method for manufacturing a polyacrylic acid (salt)-based absorbent, having a surface-crosslinking agent addition step for adding a solution of a surface-crosslinking agent, and a liquid permeation enhancer addition step for adding a liquid permeation enhancer, the liquid permeation enhancer addition step being performed after and/or at the same time as the surface-crosslinking agent addition step, the method characterized in that a surface crosslinking step for performing heat treatment in an atmosphere having a dew point of 45° C. to 100° C. is performed after or at the same time as the surface-crosslinking agent addition step.

12 Claims, 2 Drawing Sheets

(56) References Cited

U.S. PATENT DOCUMENTS

| | | |
|---|---|---|
| 2008/0281049 A1 | 11/2008 | Wendker |
| 2010/0041550 A1 | 2/2010 | Riegel |
| 2010/0072421 A1 | 3/2010 | Kitano |
| 2010/0119312 A1 | 5/2010 | Nagashima |
| 2011/0040044 A1 | 2/2011 | Motoyama |
| 2011/0042612 A1 | 2/2011 | Riegel |
| 2011/0257341 A1 | 10/2011 | Riegel |
| 2011/0319518 A1 | 12/2011 | Kadonaga et al. |
| 2012/0157625 A1 | 6/2012 | Kitano et al. |
| 2012/0157635 A1* | 6/2012 | Nogi ............... A61L 15/24 525/329.7 |
| 2012/0157650 A1 | 6/2012 | Nogi et al. |
| 2012/0172536 A1 | 7/2012 | Nogi et al. |
| 2013/0102750 A1 | 4/2013 | Watanabe et al. |
| 2014/0107293 A1 | 4/2014 | Kadonaga et al. |

FOREIGN PATENT DOCUMENTS

| | | |
|---|---|---|
| EP | 0940149 A1 | 9/1999 |
| EP | 1191051 A2 | 3/2002 |
| EP | 1824910 A2 | 6/2006 |
| JP | 64-26604 A | 1/1989 |
| JP | 4-46617 A | 2/1992 |
| JP | 2002-201290 A | 7/2002 |
| JP | 2014505151 A | 2/2014 |
| KR | 2011/0049072 A | 5/2011 |
| WO | 92/000108 A1 | 1/1992 |
| WO | 95/26209 A1 | 10/1995 |
| WO | 98/49221 A1 | 11/1998 |
| WO | 00/46260 A1 | 8/2000 |
| WO | 00/53644 A1 | 9/2000 |
| WO | 0053664 | 9/2000 |
| WO | 01/074913 A1 | 10/2001 |
| WO | 02/020068 A1 | 3/2002 |
| WO | 02/022717 A1 | 3/2002 |
| WO | 02/100451 A2 | 12/2002 |
| WO | WO 2004/096304 A1 | 11/2004 |
| WO | 2005/080479 A1 | 9/2005 |
| WO | 2006/033477 A2 | 3/2006 |
| WO | 2007/065834 A1 | 6/2007 |
| WO | 2008/092842 A1 | 8/2008 |
| WO | 2008/092843 A1 | 8/2008 |
| WO | 2008/108277 A1 | 9/2008 |
| WO | 2008/110524 A1 | 9/2008 |
| WO | 2008/120742 A1 | 10/2008 |
| WO | 2009/080611 A2 | 7/2009 |
| WO | 2009/125849 A1 | 10/2009 |
| WO | WO 2011136301 A1 | 3/2011 |
| WO | 2011/040530 A1 | 4/2011 |
| WO | 2011/117263 A1 | 9/2011 |
| WO | 2012107432 A1 | 8/2012 |

OTHER PUBLICATIONS

Modern Superabsorbent Polymer Technology, A thorough, up-to-date examination of the science and practical application of superabsorbent polymers, 1998, p. 39-44, p. 97-103, p. 197-199.

Chinese Office Action dated May 30, 2016 which issued in a corresponding Chinese Patent Applicacton No. 201380047047.7, including English translation.

International Search Report for PCT/JP2013/072207, dated Nov. 19, 2013, and English translation thereof.

Supplementary European Search Report dated Feb. 5, 2016 which issued in the corresponding EP Patent Application No. 13836672.9.

XP-002753355, Nippon Shokubai Co., Ltd., 2 pages.

XP-002753356, Nippon Shokubai Co., Ltd., 3 pages.

Chinese Office Action dated Nov. 17, 2015 which issued in the counterpart Patent Application No. 2013-80047047.7, including English translation.

* cited by examiner

METHOD FOR PRODUCING POLYACRYLIC ACID (SALT)-BASED WATER ABSORBING AGENT, AND WATER ABSORBING AGENT

This application is a divisional application of U.S. patent application Ser. No. 14/426,539, filed Mar. 6, 2015, which is based on PCT patent application Ser. No. PCT/JP2013/072207, filed Aug. 20, 2013, and which claims the benefit of Japanese patent application No. JP 2012-199923, filed Sep. 11, 2012.

TECHNICAL FIELD

The present invention relates to a method of producing a polyacrylic acid (salt)-based water absorbing agent and to the water absorbing agent. More specifically, the present invention relates to (i) a method of producing a water absorbing agent to be used for sanitary materials such as disposable diapers, sanitary napkins, and so-called incontinence pads and (ii) the water absorbing agent obtained by the method.

BACKGROUND ART

Currently, an absorbent body, which is constituted by hydrophilic tissue such as pulp and by a water absorbing agent mainly made from acrylic acid (salt) or the like, is put to widespread use in sanitary materials such as disposable diapers, sanitary napkins and incontinence pads. The absorbent body is used for the purpose of absorbing bodily fluids. In recent years, these sanitary materials such as disposable diapers and sanitary napkins have been more advanced and made thinner. Accordingly, there have been increases in (i) the amount of water absorbing agent used for a piece of sanitary material and (ii) a water absorbing agent content in an entire absorbent body constituted by a water absorbing agent, hydrophilic tissue, and the like. That is, research has been conducted on reduction in the thickness of a sanitary material without reducing the amount of water absorption by increasing the ratio of water absorbing agent contained in an absorbent body through (i) using a smaller amount of hydrophilic tissue having small bulk specific gravity and (ii) using a larger amount of water absorbing agent having excellent water absorbency and large bulk specific gravity.

Such a sanitary material, in which a water absorbing agent content is increased by decreasing the ratio of hydrophilic tissue, is preferable from the viewpoint of simply holding a liquid. However, such a sanitary material is rather problematic if distribution and spreading of a liquid when the sanitary material is actually used are taken into consideration.

When absorbing water, a large amount of water absorbing agent per unit volume turns into a softer gel-like form. This induces such a phenomenon as gel blocking which causes considerable reduction in diffusibility of a liquid in a sanitary material. As a result, part of the water absorbing agent, which part is distant from a central area of the sanitary material and is therefore difficult for the liquid to reach, does not effectively function. This prevents the effect of increasing the water absorbing agent content from being sufficiently exerted, and therefore causes an absorbing ability of the sanitary material in actual use to be much lower than a theoretical level.

In order to avoid the problem and maintain absorption property of an absorbent body, a range of the ratio between hydrophilic tissue and a water absorbing agent is inevitably limited. This puts limitations on thinning of sanitary materials.

Examples of an index by which an improvement of gel blocking in a sanitary material is evaluated encompass (i) absorbency against pressure (AAP) or performance under pressure (PUP) and (ii) saline flow conductivity (hereinafter abbreviated as "SFC"; see Patent Literature 1 and the like).

Examples of a well-known technique for improving gel blocking encompass a technique in which crosslinking densities inside and outside of a water absorbing agent are changed by surface treatment (see Patent Literatures 2 to 21). There are also known attempts to improve water absorbing ability, particularly liquid diffusibility, by combining surface treatment with, as a liquid permeability enhancer, (i) inorganic fine particles, (ii) inorganic compounds such as polyvalent metal salt, or (iii) cationic polymer compounds (see Patent Literatures 22 to 35). Furthermore, a technique for controlling a reaction environment of surface crosslinking treatment is also known (see Patent Literatures 36 to 39).

However, while the aforementioned well-known methods can prevent gel blocking, the methods also pose the following problems: (i) Liquid diffusibility, particularly saline flow conductivity (hereinafter also referred to as "SFC") and gel bed permeability (hereinafter also referred to as "GBP"), in a sanitary material does not attain desired performance. (ii) Even though SFC and GBP are sufficient, absorption capacity (CRC) and absorption capacity under load (AAP or PUP) are extremely lowered. (iii) In actual production of a water absorbing agent, performance of the water absorbing agent cannot be maintained sufficiently. For example, excellent properties of a water absorbing agent cannot be consistently obtained during production.

CITATION LIST

Patent Literatures

Patent Literature 1
Pamphlet of International Publication No. WO 95/26209
Patent Literature 2
Specification of U.S. Pat. No. 6,297,319
Patent Literature 3
Specification of U.S. Pat. No. 6,372,852
Patent Literature 4
Specification of U.S. Pat. No. 6,265,488
Patent Literature 5
Specification of U.S. Pat. No. 6,809,158
Patent Literature 6
Specification of U.S. Pat. No. 4,734,478
Patent Literature 7
Specification of U.S. Pat. No. 4,755,562
Patent Literature 8
Specification of U.S. Pat. No. 4,824,901
Patent Literature 9
Specification of U.S. Pat. No. 6,239,230
Patent Literature 10
Specification of U.S. Pat. No. 6,559,239
Patent Literature 11
Specification of U.S. Pat. No. 6,472,478
Patent Literature 12
Specification of U.S. Pat. No. 6,657,015
Patent Literature 13
Specification of U.S. Pat. No. 5,672,633
Patent Literature 14

Specification of European Patent Application Publication No. 0940149
Patent Literature 15
Pamphlet of International Publication No. WO 2006/033477
Patent Literature 16
Specification of U.S. Pat. No. 7,201,941
Patent Literature 17
Specification of U.S. Pat. No. 4,783,510
Patent Literature 18
Specification of European Patent No. 1824910
Patent Literature 19
Pamphlet of International Publication No. WO 2002/100451
Patent Literature 20
Specification of U.S. Pat. No. 5,610,208
Patent Literature 21
Pamphlet of International Publication No. WO 92/000108
Patent Literature 22
Pamphlet of International Publication No. WO 98/49221
Patent Literature 23
Pamphlet of International Publication No. WO 00/53644
Patent Literature 24
Pamphlet of International Publication No. WO 00/53664
Patent Literature 25
Pamphlet of International Publication No. WO 01/074913
Patent Literature 26
Pamphlet of International Publication No. WO 2002/020068
Patent Literature 27
Pamphlet of International Publication No. WO 2002/022717
Patent Literature 28
Pamphlet of International Publication No. WO 2005/080479
Patent Literature 29
Pamphlet of International Publication No. WO 2007/065834
Patent Literature 30
Pamphlet of International Publication No. WO 2008/092842
Patent Literature 31
Pamphlet of International Publication No. WO 2008/092843
Patent Literature 32
Pamphlet of International Publication No. WO 2008/110524
Patent Literature 33
Pamphlet of International Publication No. WO 2009/080611
Patent Literature 34
Japanese Examined Patent Application Publication, Tokukouhei, No. 4-46617
Patent Literature 35
Pamphlet of International Publication No. WO 00/46260
Patent Literature 36
Specification of European Patent No. 1191051
Patent Literature 37
Pamphlet of International Publication No. WO 2011/117263
Patent Literature 38
Pamphlet of International Publication No. WO 09/125849
Patent Literature 39
Korean Patent No. 2011/0049072A Non-Patent Literature Non-Patent Literature 1
Modern Superabsorbent Polymer Technology (1998) (particularly, p. 39 through 44, p. 97 through 103, p. 197 through 199 etc.)

SUMMARY OF INVENTION

Technical Problem

An object of the present invention is, for the purpose of solving the problems, to provide a water absorbing agent which is unlikely to cause gel blocking and is suitable for a thin sanitary material/absorbent article containing a large amount of water absorbing agent, and which (i) has excellent liquid diffusibility (e.g. SFC and GBP) as a result of addition of a liquid permeability enhancer and (Ii) has absorption capacity under load (e.g. AAP and PUP) that is decreased only by a small amount even if the liquid permeability enhancer is added. The object of the present invention is also to provide a method of stably producing the water absorbing agent in actual production.

It is also the object of the present invention to provide a method of evaluation of strength of a surface-crosslinked layer of a water absorbing agent, quantification of which evaluation with a simple process has been conventionally difficult.

Solution to Problem

The inventors of the present invention conducted diligent research to solve the problems, and found that a decrease in absorption capacity under load as a result of addition of a liquid permeability enhancer is closely related to how a surface-crosslinked layer is formed. That is, the inventors considered that in a case where a water absorbing agent has a surface-crosslinked layer that is strong enough not to be easily broken as a result of swelling of the water absorbing agent as a result of water absorption, the decrease in absorption capacity under load as a result of addition of a liquid permeability enhancer can be restricted.

In other words, the inventors of the present invention considered that there is a correlation between strength of a surface-crosslinked layer and surface soluble component which is measured under particular conditions. Then the inventors found that a water absorbing agent having a smaller amount of surface soluble component has a stronger surface-crosslinked layer.

Then, the inventors found that it is possible to stably obtain a water absorbing agent of the present invention by carrying out, in a particular environment in which an atmospheric dew point is 45° C. to 100° C., a heat treatment on a water absorbent resin containing a surface crosslinking agent, the heat treatment being carried out in a surface crosslinking step which is one of the steps involved in a process of producing a water absorbing agent containing a polyacrylic acid (salt)-based water absorbent resin containing a liquid permeability enhancer. The present invention has been thus completed.

The present invention is a method for producing a polyacrylic acid (salt)-based water absorbing agent, comprising: a surface crosslinking agent addition step of adding a surface crosslinking agent solution; a liquid permeability enhancer addition step of adding a liquid permeability enhancer, the liquid permeability enhancer addition step being performed simultaneously with and/or after the surface crosslinking agent addition step; and a surface crosslinking step of carrying out a heat treatment in conditions in which an atmospheric dew point is in a range of 45° C. to 100° C., the surface crosslinking step being performed simultaneously with or after the surface crosslinking agent addition step.

Advantageous Effects of Invention

With the method of producing the water absorbing agent of the present invention, it is possible to obtain a water absorbing agent having a surface-crosslinked layer that is highly liquid-permeable and is unlikely to break even when the water absorbing agent swells. In a case of commercial-scale production of the water absorbing agent, the method also makes it easy to design a manufacturing device used particularly in the surface crosslinking step or after the surface crosslinking step and to set operation conditions. Even in a case where a liquid permeability enhancer is added in order to obtain the water absorbing agent by the production method of the present invention, the water absorbing agent thus obtained is an excellent water absorbing agent which has absorption capacity under load that is decreased only by a small amount, and possesses both high liquid permeability and high absorption capacity under load.

According to the production method of the present invention, an increase in liquid permeability becomes significantly large in a case where a cationic polymer compound is used as a liquid permeability enhancer.

DESCRIPTION OF EMBODIMENTS

Figure 1:
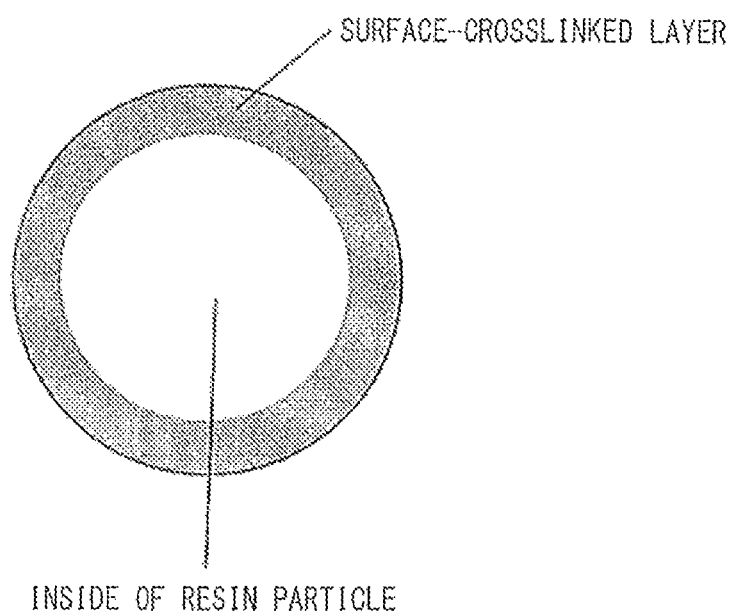
FIG. 1 is a cross-sectional view illustrating a model of a water absorbent resin after being subjected to surface crosslinking. The cross-sectional view schematically illustrates the water absorbent resin having a surface-crosslinked layer formed thereon.

Hereinafter, a method for producing a polyacrylic acid (salt)-based water absorbing agent according to the present invention will be described in detail. It should be noted that the scope of the present invention is not limited to the description and can be embodied with modifications other than the following exemplary embodiments but not departing from the gist of the present invention. More specifically, the present invention shall not be construed as being limited to the following embodiments, may be modified in many ways within the scope of the following claims. The technical scope of the present invention can encompass any modifications obtainable by appropriately combining technical means disclosed in different embodiments. Moreover, in the present invention, the terms "weight" and "mass", "wt %" and "mass %", and "parts by weight" and "parts by mass" are synonymous with each other correspondingly, and the terms "mass", "mass %", and "parts by mass" are used herein for consistency.

[1] Definitions of Terms (1-1) Water Absorbing Agent

The term "water absorbing agent" as used herein means a gelatinizer for an aqueous liquid, which gelatinizer contains a water absorbent resin of not less than 70 mass %, preferably not less than 85 mass %, obtained by subjecting a water absorbent resin to a surface crosslinking step and a step of adding a liquid permeability enhancer (hereinafter also referred to as "liquid permeability enhancer addition step"). Not only a surface crosslinking agent and the liquid permeability enhancer, but also a chelating agent, a reducing agent, an antioxidant, an anti-coloring agent, etc. each in an amount of 0 to 10 mass %, preferably 0.1 to 1 mass %, may be added to or contained in the water absorbent resin.

(1-2) Surface-crosslinked Water Absorbent Resin

The term "surface-crosslinked water absorbent resin" as used herein means a gelatinizer for an aqueous solution, which gelatinizer is obtained by subjecting a water absorbent resin to the surface crosslinking step. A product obtained by subjecting a water absorbent resin to the surface crosslinking step after the surface crosslinking agent addition step and the liquid permeability enhancer addition step is also referred to as "surface-crosslinked water absorbent resin."

(1-3) "Polyacrylic Acid (Salt)-based Water Absorbent Resin"

The term "water absorbent resin" as used herein means a water-swellable or water-insoluble polymer gelatinizer. Note that the "water-swellable" property is a property of having CRC (centrifuge retention capacity), of not less than 5 [g/g], where the CRC is defined in ERT 441.2-02, and the "water-insoluble" property is a property of having Extr (water soluble component) of 0 mass % to 50 mass %, where the Extr is defined in ERT 470.2-02.

The water absorbent resin is not limited to a resin in which the water absorbent resin is totally a polymer (100 mass %), and therefore can be the one that contains an additive or the like, provided that the above "water-swellable" and "water-insoluble" properties are ensured. A water absorbent resin composition containing a small amount of additive is also referred collectively to as the water absorbent resin in accordance with the present invention. Moreover, the form of the water absorbent resin is not particularly limited. Examples of the form of the water absorbent resin include a sheet form, a fiber form, a film form, a gel form, a powder form, and the like. The water absorbent resin is preferably in the form of powder, particularly preferably in the form of powder having the particle size and moisture content, both of which will be described later. Such a water absorbent resin may be referred to as a water absorbent resin powder.

The term "polyacrylic acid (salt)-based water absorbent resin" as used herein means a polymer that optionally has a graft component and contains, as main components, recurring units constituted by an acrylic acid and/or a salt thereof (hereinafter referred to as acrylic acid (salt)).

More specifically, the "polyacrylic acid (salt)-based water absorbent resin" as used in the present invention is a polymer in which acrylic acid (salt) accounts for 50 mol % to 100 mol % in the total monomer content (except a crosslinking agent) to be polymerized, preferably a water absorbent resin in which acrylic acid (salt) accounts for 70 mol % to 100 mol % in the total monomer content, more preferably a water absorbent resin in which acrylic acid (salt) accounts for 90 mol % to 100 mol % in the total monomer content, and particularly preferably a water absorbent resin in which acrylic acid (salt) accounts for substantially 100 mol % in the total monomer content. Moreover, in the present invention, a polyacrylate (neutralized) polymer is also referred collectively to as "polyacrylic acid (salt)-based water absorbent resin".

(1-4) "EDANA" and "ERT"

The term "EDANA" stands for European Disposables and Nonwovens Associations. The term "ERT" stands for EDANA Recommended Test Methods, which is the European-standard (actually the global-standard) method of measuring water absorbent resins. The ERT is a method of measuring the physical properties of water absorbent resins, and unless otherwise specified, the measurement of the physical properties of the water absorbent resin herein is carried out in conformity with a master copy of the ERT (Known Literature: 2002 revised version).

(a) "CRC" (ERT441.2-02)

The term "CRC" stands for a centrifuge retention capacity and means absorption capacity without load (hereinafter may be referred simply to as "absorption capacity"). Specifically, the "CRC" means absorption capacity (Unit: [g/g]) observed when 0.200 g of water absorbent resin wrapped in unwoven cloth is allowed to freely swell in a 0.9 mass % of sodium chloride aqueous solution (physiological saline) without load for 30 minutes and then drained by a centrifugal machine.

(b) "AAP" (ERT442.2-02)

The term "AAP" stands for Absorption Against Pressure and means absorption capacity under load. Specifically, the "AAP" means absorption capacity (Unit: [g/g]) observed after 0.900 g of water absorbent resin is allowed to swell in a 0.9 mass % of sodium chloride aqueous solution (physiological saline) under a load for 1 hour. It should be noted that the measurement of the AAP herein is different from the ERT 442.2-02 in that the AAP is measured under a load of 4.83 kPa (0.7 psi).

(C) "0.58 psi PUP"

The term "0.58 psi PUP" as used herein stands for Performance Under a Pressure of 0.58 psi (4.12 kPa), and means absorption capacity under load relative to artificial urine. Specifically, what is meant by the term is identical to absorption capacity (unit: [g/g]) measured according to the PUP measuring method disclosed in the pamphlet of International Publication No. WO 95/26209, except that pressure applied is 4.12 kPa (0.58 psi).

(d) "Extr." (ERT470.2-02)

The term "Extr." stands for Extractables, and means water soluble component (water soluble component amount). Specifically, Extr. is water soluble component (unit: mass %) measured by mixing 1.000 g of water absorbent resin in 200 g of 0.9 mass % of sodium chloride aqueous solution for 16 hours, and then measuring an amount of polymer dissolved therein by pH titration.

(e) "PSD" (ERT420.2-02)

The term "PSD" stands for Particle Size Distribution and means a particle size distribution measured by sieve classification. It should be noted that the mass average particle diameter (D50) and the distribution of particle diameter are measured by the method as set forth in "Average Particle Diameter and Distribution of Particle Diameter" of U.S. Patent No. 2006/204755.

(1-5) Surface Soluble Component

The term "surface soluble component" is soluble component (unit: mass %) obtained by (i) adding 1.00 g of water absorbent resin to 25 g of a 0.90 mass % of sodium chloride aqueous solution (physiological saline) to bring about swell, (ii) allowing a resultant mixture to stand for 1 hour, (iii) adding 75 g of 0.90 mass % saline to the mixture and stirring for 1 minute, (iv) filtering a resultant mixture, and (v) measuring soluble component (unit: mass %) that has been seeped from the periphery of a surface of the resin. The surface soluble component is calculated by measuring, as is the case of Extr. in (d) described above, an amount of dissolved polymer by pH titration.

The water soluble component described in (d) above and the present surface soluble component differ in that the water soluble component described in (d) above is obtained by extracting a soluble component from an entire resin through stirring the resin in a large excess of physiological saline for 16 hours, whereas the present surface soluble component is measured by causing a resin to seep into physiological saline through rinsing the resin for 1 minute while the resin is swollen with an absorption capacity of 25 g/g. (Note, however, that the present surface soluble component is likewise measured even in a case where the absorption capacity is less than 25 g/g.)

It is generally known that surface crosslinking causes absorption capacity on a surface of a resin particle to differ from absorption capacity inside the resin particle, and that the absorption capacity of a surface-crosslinked layer, which is more cross-linked than the inside of the resin particle, is smaller than the absorption capacity inside the particle. It is also known that a surface-crosslinked layer, because of its high crosslinking density property, restricts seeping of a soluble component of an entire particle. That is, the surface soluble content is considered highly affected by the state of the surface-crosslinked layer which is formed in the surface crosslinking step.

Figure 2:
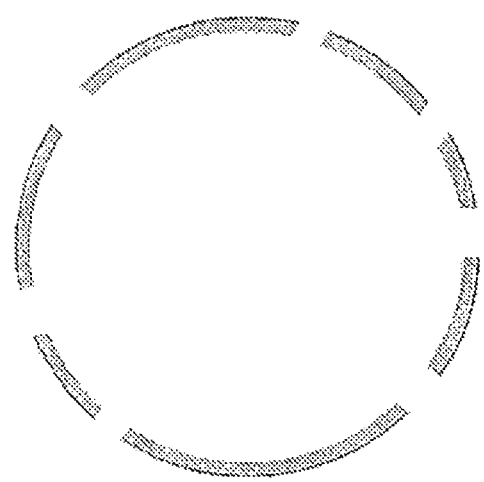
FIG. 2 is a cross-sectional view illustrating a model of a water absorbent resin whose surface-crosslinked layer is broken as a result of swelling caused by water absorption.
Figure 3:
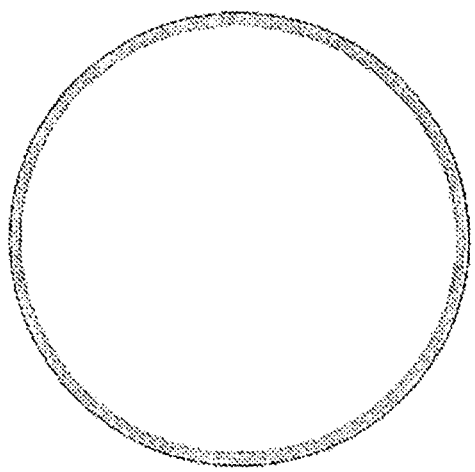
FIG. 3 is a cross-sectional view illustrating a model of a water absorbent resin whose surface-crosslinked layer is not broken as a result of swelling caused by water absorption.

Specifically, a water absorbent resin swells due to a volume increase as a result of water absorption. In a case where the water absorbent resin swells beyond a maximum allowable limit of a surface-crosslinked layer, the surface-crosslinked layer breaks as illustrated in FIG. 2. This causes an inside soluble component to seep out to a surface through broken regions. On the other hand, in a case where a surface-crosslinked layer is strong, the surface-crosslinked layer is unlikely to break (see FIG. 3) even if the water absorbent resin swells to increase in volume, so that it is considered that surface soluble component is small.

(1-6) Surface-crosslinked Layer Strength Index

The term "surface-crosslinked layer strength index" as used in the present invention means a value obtained by multiplying, by 100 times, a value obtained through dividing the surface soluble component (%) by Extr (%). described in (d) above. In other words, the surface-crosslinked layer strength index is a value that indicates a proportion of, to an entire soluble component (%), a soluble component (%) seeping from the periphery of a surface under the particular conditions (standing for 1 hour while swelling 25-fold/real-life use model of a diaper). The surface-crosslinked layer strength index thus indicates how efficiently a surface-crosslinked layer restricts seeping of an entire soluble component during actual use of a diaper or the like.

In other words, the surface-crosslinked layer strength index as used in the present invention is an index that indicates a degree to which a surface-crosslinked layer is broken by water absorption or swelling. It is considered that if the index is small, a surface-crosslinked layer, which is strong enough to restrict seeping of soluble component even during actual use, is formed.

Since the conventional method of measuring soluble component is carried out by dispersing a water absorbent resin in a large excess of water and then extracting entire soluble component, the conventional method can hardly be said to properly evaluate conditions of actual use of a diaper or the like. In contrast, it is possible with the surface-crosslinked layer strength index of the present invention to precisely evaluate a surface-crosslinked layer, and it is therefore possible to attain the object of the present invention.

(1-7) "Liquid Permeability"

The degree of flowing of a liquid between particles of swollen water absorbent resin under load or without load is referred to as "liquid permeability". The "liquid permeability" is measured typically as SFC (Saline Flow Conductivity) or GBP (Gel Bed Permeability).

"SFC (Saline Flow Conductivity)" is liquid permeability of 0.9 g of water absorbent resin for a 0.69 mass % of sodium chloride aqueous solution under load of 2.07 kPa, and is measured according to the SFC test method disclosed in the specification of U.S. Pat. No. 5,669,894. Moreover, "GBP" is liquid permeability of a water absorbent resin for a 0.69 mass % of sodium chloride aqueous solution wherein the water absorbent resin is under load or allowed to freely swell, and is measured according to the GBP test method disclosed in the International Publication No. WO 2005/016393.

(1-8) Others

The expression "X to Y" for expression of a range herein means "not less than X and not more than Y" in which both X and Y are inclusive. Moreover, the weight unit "t (ton)" means "Metric ton". Further, unless otherwise specified, "ppm" means "ppm by mass". Further, the wording " . . . acid (salt)" means " . . . acid and/or salt thereof". The wording "(meth)acrylic" means "acrylic and/or methacrylic". Besides, unless otherwise specified, physical properties and the like are measured at room temperature (20 to 25° C.) at a relative humidity of 40 to 50% RH.

[2] A Process for Production of Polyacrylic Acid (Salt)-based Water Absorbent Resin Powder (2-1) Step of Preparing Acrylic Acid (Salt)-based Monomer Aqueous Solution As used herein, the term "acrylic acid (salt)-based monomer aqueous solution" is an aqueous solution of a monomer(s) (hereinafter referred to as "monomer aqueous solution") which are mainly acrylic acid (salt). The acrylic acid (salt)-based monomer aqueous solution may contain, if necessary, constituent components of the water absorbent resin powder, such as a crosslinking agent, a graft component, a minute component (chelating agent, surfactant, a dispersing agent, or the like). It is possible to perform the polymerization with the acrylic acid (salt)-based monomer aqueous solution as such and a polymerization initiator added thereto.

The acrylic acid (salt) may be not neutralized or may be a salt (fully neutralized or partially neutralized). Moreover, the monomer aqueous solution may exceed its saturation concentration. The acrylic acid (salt)-based monomer aqueous solution in the present invention also encompasses a supersaturated aqueous solution or a slurry aqueous solution (aqueous dispersion solution) of the acrylic acid (salt). From the viewpoint of physical properties of the resultant water absorbent resin powder, it is preferable that the acrylic acid (salt)-based monomer aqueous solution not saturated is used.

A solvent for the monomer(s) is preferably water. In a case where the solvent for the monomer(s) is water, an acrylic acid (salt)-based monomer is dealt as an aqueous solution. The term "aqueous solution" as used herein is not limited to a solution containing water of 100 mass % as a solvent and may contain, as the solvent, a combination of water and a water-soluble organic solvent (e.g. alcohol etc.) of 0 mass % to 30 mass %, preferably 0 mass % to 5 mass %. These are dealt herein as "aqueous solutions."

As used herein, the term "partly-prepared acrylic acid (salt)-based monomer aqueous solution" refers to an aqueous solution of acrylic acid (salt), which is to be prepared as a monomer aqueous solution whose main component is acrylic acid and/or its salt, but to which not all constituent components have been added. Specifically, the partly-prepared acrylic acid (salt)-based monomer aqueous solution includes an acrylic acid aqueous solution and a fully or partly neutralized acrylic acid salt aqueous solution.

The partly-prepared acrylic acid (salt)-based monomer aqueous solution is to be further neutralized, mixed with water as a solvent, or mixed with the minute component(s), thereby being prepared as the fully prepared acrylic acid (salt)-based monomer aqueous solution. It should be noted that the fully prepared acrylic acid (salt)-based monomer aqueous solution, when it is in such a state that it has not been introduced into a polymerizer or has been introduced into the polymerizer but whose polymerization has not been started yet, is referred to as "pre-polymerization fully prepared acrylic acid (salt)-based monomer aqueous solution".

(Monomer)

The acrylic acid (salt)-based monomer according to the present invention is not particularly limited, provided that a water absorbent resin can be produced therefrom by polymerization, and examples thereof encompasses: anionic unsaturated monomers and salt thereof such as (meth)acrylic acid, (anhydrous)maleic acid, itaconic acid, cinnamic acid, vinylsulfonic acid, allyltoluenesulfonic acid, vinyltoluene sulfonic acid, styrene sulfonic acid, 2-(meth)acrylamide-2-methylpropanesulfonic acid, 2-(meth)acryloyl ethanesulfonic acid, 2-(meth)acryloyl propanesulfonic acid, and 2-hydroxyethyl (meth)acryloyl phosphate; mercapto group-containing unsaturated monomers; phenolic hydroxide group-containing unsaturated monomers; amide group-containing unsaturated monomers such as (meth)acrylamide, N-ethyl (meth) acrylamide, N,N-dimethyl (meth)acrylamide; amino group-containing unsaturated monomers such as N,N-dimethylamino ethyl (meth)acrylate, N,N-dimethylaminopropyl (meth)acrylate, and N,N-dimethylaminopropyl (meth)acrylamide; and the other monomers.

The content (used amount) of the acrylic acid (salt)-based monomer is normally not less than 50 mol %, preferably not less than 70 mol %, more preferably not less than 80 mol %, still more preferably not less than 90 mol %, and particularly preferably not less than 95 mol % (upper limit is 100 mol %), relative to a total monomer content (excluding an internal crosslinking agent). It should be noted that the polyacrylic acid (salt) according to the present invention, which is not limited to a non-neutralized one (0 mol % neutralization rate), is defined as encompassing a partially neutralized or fully neutralized one (100 mol % neutralization rate).

A neutralization rate of the acrylic acid (salt)-based monomer or the water-containing gel-like crosslinked polymer after the polymerization according to the present invention is not particularly limited to a specific neutralization rate, but is preferably in a range of 40 mol % to 90 mol %, more preferably in a range of 50 mol % to 80 mol %, and still more preferably in a range of 60 mol % to 74 mol %, from the viewpoint of physical properties of a resultant water absorbent resin powder or reactivity of the surface crosslinking agent.

It is preferable that the neutralization rate is within these ranges, because a low neutralization rate tends to lower a water absorbing speed (for example, FSR) of a resultant water absorbent resin, and a high neutralization rate tends to lower reactivity of the polyacrylic acid (salt)-based water absorbent resin powder with a surface crosslinking agent, particularly with a dehydration reaction surface crosslinking agent described later, thereby resulting in low yield of a water absorbent resin or low liquid permeability (for example, SFC) and low absorption capacity under load (for example, AAP or PUP) of the water absorbent resin.

The acrylic acid (salt)-based monomer or the water-containing gel-like crosslinked polymer may be partly or totally salt from the viewpoint of the absorption capacity without load (CRC) and the absorption capacity under load (AAP and PUP) of a water absorbing agent obtained as a final product. The acrylic acid (salt)-based monomer or the water-containing gel-like crosslinked polymer is preferably monovalent salts such as alkaline metal salt (sodium salt, lithium salt, and potassium salt), ammonium salt, and amines. Among them, the acrylic acid (salt)-based monomer or the water-containing gel-like crosslinked polymer is more preferably alkaline metal salt, still more preferably sodium salt and/or potassium salt, and particularly preferably sodium salt from the viewpoint of cost and physical property.

(Polymerization Inhibitor)

The acrylic acid (salt)-based monomer according to the present invention contains a polymerization inhibitor. Although the polymerization inhibitor is not particularly limited, examples of the polymerization inhibitor encompass N-oxyl compounds, manganese compounds, substituted phenol compounds, and the like, which are disclosed in International Publication No. WO 2008/096713. Among these compounds, the substituted phenol compounds are preferable, and among the substituted phenol compounds, methoxy phenols are particularly preferable.

Examples of the methoxy phenols encompass o, m, p-methoxy phenol, methoxy phenols substituted with one or more substituents such as a methyl group, a t-butyl group, or a hydroxyl group, and the like. In the present invention, p-methoxy phenol is particularly preferable.

The polymerization inhibitor content in the acrylic acid (salt)-based monomer is preferably in a range of 10 ppm to 200 ppm, more preferably in a range of 5 ppm to 160 ppm, 10 ppm to 160 ppm, 10 ppm to 100 ppm, 10 ppm to 80 ppm, in this order, and most preferably in a range of 10 ppm to 70 ppm, relative to a total amount of the acrylic acid (salt)-based monomer. If the polymerization inhibitor content of more than 200 ppm, deterioration in color tone (yellowing, yellow color change) may occur on the resultant water absorbing agent. If the polymerization inhibitor content is less than 5 ppm, that is, if the polymerization inhibitor is removed due to refining such as distillation or the like, unintentional polymerization may take place.

(Internal Crosslinking Agent)

In the present invention, at the polymerization, an internal crosslinking agent is used if necessary. The internal crosslinking agent is not particularly limited and can be a publicly known internal crosslinking agent. Examples of the internal crosslinking agents encompass: N,N'-methylenebis (meth) acrylamide, (poly)ethylene glycol di(meth)acrylate, (poly) propyleneglycol di(meth)acrylate, trimethylolpropane tri (meth)acrylate, glycerine tri(meth)acrylate, glycerine acrylate methacrylate, ethyleneoxide modified trimethylol propane tri(meth)acrylate, pentaerythritol hexa(meth)acrylate, triallyl cyanurate, triallyl isocyanurate, triallyl phosphate, triallylamine, poly(meth)allyloxy alkanes, (poly)ethylene glycol diglycidyl ether, glycerol diglycidyl ether, ethylene glycol, polyethylene glycol, propylene glycol, glycerin, 1,4-butanediol, pentaerythritol, ethylenediamine, ethylene carbonate, propylene carbonate, polyethyleneimine, glycidyl (meth)acrylate, and the like. In consideration of reactivity, one or more kinds of compounds among them can be used. Especially, it is preferable to use a compound having two or more polymerizable unsaturated groups.

Further, in a case where two or more internal crosslinking agents are used in combination, an internal crosslinkage structure can be changed by changing reactivity of functional groups of the internal crosslinking agents. As such, it is preferable that internal crosslinking agents having different functional groups are selected for use in combination from among amide compounds, (meth)acrylate compounds, allylic compounds, amine compounds, imine compounds, alcohol compounds, carbonate compounds, and glycidyl compounds.

A used amount of the internal crosslinking agent can be determined as appropriate, depending on desired physical properties of the water absorbing agent. However, the used amount of the internal crosslinking agent is preferably in a range of 0.001 mol % to 5 mol %, more preferably in a range of 0.005 mol % to 2 mol %, and still more preferably in a range of 0.01 mol % to 1 mol %, relative to a total amount of the acrylic acid (salt)-based monomer(s). If two or more internal crosslinking agents are used in combination, the used amount of each of the internal crosslinking agents is preferably in a range of 0.001 mol % to 5 mol %, more preferably in a range of 0.005 mol % to 2 mol %, and still more preferably in a range of 0.01 mol % to 1 mol %, relative to a total amount of the acrylic acid (salt)-based monomer(s).

If the used amount of the internal crosslinking agent (or a total amount of the two or more internal crosslinking agents used in combination) is less than 0.001 mol %, a resultant water absorbing agent has a high water soluble component, thereby resulting in a risk of failing to ensure a sufficient absorbing amount under load. On the other hand, if the used amount of the internal crosslinking agent exceeds 5 mol %, this would possibly result in a high crosslinking density of a resultant water absorbing agent, thereby resulting in an insufficient absorbing amount of the resultant water absorbing agent. It should be noted that the internal crosslinking agent(s) may be added in whole to the pre-polymerization fully prepared acrylic acid (salt)-based monomer aqueous solution, or a portion thereof may be added after the polymerization is initiated.

(Dispersing Agent)

The dispersing agent usable in the present invention is not particularly limited, but is preferably a water absorbent polymer dispersing agent, a hydrophilic polymer dispersing agent that is water absorbable, or a water-soluble polymer dispersing agent, and more preferably the water-soluble polymer dispersing agent. A weight average molecular weight of the dispersing agent is determined as appropriate depending on the type of the dispersing agent. However, the weight average molecular weight of the dispersing agent is preferably in a range of 500 to 10,000,000, more preferably in a range of 5,000 to 5,000,000, and particularly preferably in a range of 10,000 to 3,000,000.

The dispersing agent is not limited to a specific kind of dispersing agent. Examples of the dispersing agent encompass hydrophilic polymers such as starch, a starch derivative, cellulose, cellulose derivative, polyvinyl alcohol (PVA), carboxymethyl cellulose (sodium), hydroxyethyl cellulose, polyacrylic acid (salt), and crosslinked polyacrylic acid (salt). Among them, a water-soluble polymer dispersing agent selected from starch, cellulose, and PVA is preferable from the viewpoint of not impairing hydrophilicity of the water absorbing agent of the present invention.

A used amount of the dispersing agent is preferably in a range of 0 part by mass to 50 parts by mass, more preferably in a range of 0.01 parts by mass to 20 parts by mass, still more preferably in a range of 0.05 parts by mass to 10 parts by mass, and specifically preferably in a range of 0.1 parts by mass to 5 parts by mass, relative to 100 parts by mass of the acrylic acid (salt)-based monomer. The use of more than 50 parts by mass of the dispersing agent may decrease absorption property of the water absorbing agent.

(2-2) Polymerization Step (Polymerization Method)

A polymerization method for obtaining a water absorbent resin powder according to the present invention is exemplified by spraying polymerization, droplet polymerization, bulk polymerization, precipitation polymerization, aqueous polymerization, reverse-phase suspension polymerization, and other polymerizations. In order to achieve the object of the present invention, it is preferable to employ aqueous polymerization or reverse-phase suspension polymerization, each of which is carried out by using an aqueous solution of monomers.

The aqueous polymerization is a method of polymerizing a monomer aqueous solution without using a dispersion solvent. Such aqueous polymerization is any of the polymerization methods disclosed in, for example, U.S. Pat. Nos. 4,625,001, 4,873,299, 4,286,082, 4,973,632, 4,985,518, 5,124,416, 5,250,640, 5,264,495, 5,145,906, 5,380,808, and European Patent No. 0811636, European Patent No. 0955086, European Patent No. 0922717, and others.

The reverse-phase suspension polymerization is a method of carrying out polymerization by suspending a monomer aqueous solution in a hydrophobic organic solvent. Such reverse-phase suspension polymerization is any of the polymerization methods disclosed in, for example, U.S. Pat. Nos. 4,093,776, 4,367,323, 4,446,261, 4,683,274, 5,244, 735, and others. The monomers, the polymerization initiators, etc. disclosed in these patent literatures are applicable to the reverse-phase suspension polymerization in the present invention.

The concentration of the monomer aqueous solution in the polymerization is not particularly limited, but is preferably in a range of 20 mass % to the saturated concentration, more preferably in a range of 25 mass % to 80 mass %, and still more preferably in a range of 30 mass % to 70 mass %. The monomer concentration of less than 20 mass % may decrease productivity. It should be noted that polymerization with a monomer slurry (aqueous dispersion of acrylate) results in polymers with poor properties. Thus, the polymerization is preferably carried out with a monomer concentration not more than the saturated concentration (see Japanese Patent Application Publication, Tokukaihei, No. 1-318021).

In order to promote the polymerization and to thereby improve the physical properties of a water absorbing agent, the step of degassing the dissolved oxygen (for example, the step of exchanging the dissolved oxygen with inert gas) may be provided if necessary during the polymerization. In addition, for the purpose of increasing the water absorbing speed of a water absorbing agent, increasing a surface area of the water absorbing agent, increasing drying speed of the water absorbing agent, or the like, air bubbles (particularly inert gas) or various kinds of foaming agents (for example, organic or inorganic carbonate, an azo compound, a urea compound) may be contained during the polymerization so that foams are formed so as to increase to, for example, 1.001 to 10 times by volume during the polymerization and during the drying.

Further, in order to promote foaming during the polymerization and to improve handling property such as fluidity of a resultant polymerized gel, a surfactant, which is different from another surfactant described later, may be added to a monomer aqueous solution before the polymerization step and/or during the polymerization step. As the surfactant used for this purpose, the surfactant described in paragraphs [0115] to [0123] of the pamphlet of International Publication No. WO 2011/078298 can be employed.

The polymerization in the present invention can be carried out under any of normal atmospheric pressure, reduced pressure, and increased pressure. Preferably, the polymerization is carried out under the normal atmospheric pressure (101.3 kPa (1 atmospheric pressure)) (or under an atmospheric pressure close to the normal atmospheric pressure (normal atmospheric pressure—10%)). Depending upon the type of polymerization initiator to be used, the temperature at the initiation of polymerization is preferably in a range of 15° C. to 130° C. and more preferably in a range of 20° C. to 120° C.

(Polymerization Initiator)

A polymerization initiator used in the present invention is selected appropriately depending on a polymerization scheme, and is not particularly limited. Examples of the polymerization initiator include photodegradable polymerization initiators, pyrolytic polymerization initiators, redox polymerization initiators, and the like. With any of these polymerization initiators, polymerization in the present invention is initiated.

Examples of the photodegradable polymerization initiators encompass benzoin derivatives, benzyl derivatives, acetophenone derivatives, benzophenone derivatives, azo compounds, and the like.

Examples of the pyrolytic polymerization initiators encompass: persulfates such as sodium persulfate, potassium persulfate, and ammonium persulfate; peroxides such as hydrogen peroxide, t-butyl peroxide, and methyl-ethylketone peroxide; azo compounds such as 2,2'-azobis (2-amidinopropane)dihydrochloride, and 2,2'-azobis (2-(2-imidazoline 2-yl)propane)dihydrochloride; and the like.

Examples of the redox polymerization initiators encompass systems each of which is a combination of (i) a reducing compound such as L-ascorbic acid or sodium hydrogen sulfite and (ii) the foregoing persulfate or peroxide.

Further, it is also a preferable embodiment to use the photodegradable polymerization initiator and the pyrolytic polymerization initiator in combination. Still further, an active energy ray such as an ultraviolet ray, an electron ray, or a gamma ray may be used alone or used in combination with the polymerization initiator.

The amount of the polymerization initiator to be used is preferably in a range of 0.0001 mol % to 1 mol %, and more preferably in a rage of 0.0005 mol % to 0.5 mol %, relative to the total amount of the monomers. The polymerization initiator used in an amount of more than 1 mol % may cause deterioration in color tone of water absorbent resin powder.

Further, the polymerization initiator used in an amount of less than 0.0001 mol % may increase residual monomers.

(More Preferable Polymerization Method)

As the polymerization method of an acrylic acid (salt)-based monomer aqueous solution according to the present invention, at least one of reverse-phase suspension polymerization, spraying polymerization, droplet polymerization, and aqueous polymerization, and particularly aqueous polymerization, are employed from the viewpoint of physical properties (for example, water absorbing speed and liquid permeability) of water absorbent resin powder and polymerization controllability, and others.

Examples of a preferable aspect of the aqueous polymerization encompass high-temperature starting aqueous polymerization, high-concentration aqueous polymerization, and high-concentration high-temperature starting aqueous polymerization. The high-temperature starting aqueous polymerization is such that a polymerization starting temperature is preferably not lower than 40° C., more preferably not lower than 50° C., still more preferably not lower than 65° C., particularly preferably not lower than 70° C., and most preferably not lower than 80° C. (upper limit is a boiling point). The high-concentration aqueous polymerization is such that a monomer concentration is preferably not less than 40 mass %, more preferably not less than 45 mass %, and still more preferably not less than 50 mass % (upper limit is not more than 90 mass %, preferably not more than 80 mass %, and more preferably not more than 70 mass %). The high-concentration high-temperature starting aqueous polymerization is the combination of the high-temperature starting aqueous polymerization and the high-concentration aqueous polymerization.

As a polymerization scheme to be employed, kneader polymerization or belt polymerization is preferable. Examples of a preferable scheme of aqueous polymerization encompass continuous belt polymerizations (disclosed in U.S. Pat. Nos. 4,893,999, 6,241,928, U.S. Patent Application Publication No. 2005/215734, a pamphlet of International Publication No. WO 2008/114847, etc.), continuous kneader polymerization, batch kneader polymerizations (U.S. Pat. Nos. 6,987,151, 6,710,141, a pamphlet of International Publication No. WO 2008/114848, etc.), and the like.

Further, high-temperature starting continuous aqueous polymerization, high-concentration continuous aqueous polymerization, and high-concentration high-temperature starting continuous aqueous polymerization, all of which are combinations of the preferable aspects and the preferable polymerization schemes, can be exemplified.

As another preferable example, batch polymerization or continuous kneader polymerization such that the polymerization starting temperature is not lower than 15° C. and that the monomer concentration is not lower than 30 mass % can be exemplified.

Moreover, in carrying out the polymerization, a polymerization starting time (a time period between the addition of the polymerization initiator and the initiation of polymerization) is preferably more than 0 second but not more than 300 seconds, and more preferably in a range of 1 second to 240 seconds.

By employing the aforementioned aqueous polymerization, it is possible to produce water absorbent resin powder with high productivity. It should be noted that the above polymerization methods are preferably employed in a huge-scale manufacturing device whose production amount per line is large. The production amount is preferably not less than 0.5 [t/hr], more preferably not less than 1 [t/hr], still more preferably not less than 5 [t/hr], and particularly preferably not less than 10 [t/hr].

(2-3) Gel-crushing Step

The present step is an optional step of carrying out gel-crushing of a water-containing gel-like crosslinked polymer (hereinafter referred to as "hydrogel") obtained through the polymerization step, etc. (particularly, aqueous polymerization), thereby obtaining a particulate hydrogel (hereinafter referred to as "particulate hydrogel").

The hydrogel obtained through the aqueous polymerization is gel-crushed, especially by mixing and kneading for grain refining, in order to attain both of water absorbing speed and liquid permeability of a resultant water absorbent resin and to further improve impact resistance of the resultant water absorbent resin. That is, in order to attain the object of the present invention, it is preferable to adopt the aqueous polymerization rather than the reverse-phase suspension polymerization in which the gel-crushing is not necessary. It is particularly preferable to adopt the aqueous polymerization such that gel-crushing is carried out during polymerization (for example, kneader polymerization) or after polymerization (for example, belt polymerization, and, if necessary kneader polymerization).

A gel-crushing device applicable to the present invention is not particularly limited but is, for example, batch-type or continuous gel crusher having a plurality of rotational stirring blades such as double-armed kneader, a single- or twin-screwed extruders, meat chopper, etc. can be adopted. Among them, a screwed extruder having a porous plate at an end is preferable. Examples of the screwed extruder having a porous plate at an end encompass a screwed extruder disclosed in Japanese Patent Application Publication, Tokukai, No. 2000-63527.

In the gel-crushing step of the present invention, a temperature of the hydrogel (gel temperature) before gel-crushing is preferably in a range of 60° C. to 120° C., and more preferably in a range of 65° C. to 110° C., from the viewpoint of particle size control of a particulate hydrogel and physical properties of a water absorbent resin. A gel temperature lower than 60° C. results in a greater hardness of the resultant hydrogel due to the property of a hydrogel, thereby making it difficult to control the particle shape and particle size distribution in gel-crushing. Moreover, a gel temperature higher than 120° C. results in a greater softness of the resultant hydrogel, thereby making it difficult to control the particle shape and particle size distribution. It should be noted that the gel temperature can be controlled by a temperature during the polymerization, heating after the polymerization, cooling after the polymerization, or others.

Further, mass average particle diameter (D50) (defined by sieve classification) of a particulate hydrogel after the gel-crushing is preferably in a range of 0.5 mm to 3 mm, more preferably in a range of 0.6 mm to 2 mm, and still more preferably in a range of 0.8 mm to 1.5 mm. Moreover, the proportion of a coarse particulate hydrogel of not less than 5 mm in particle diameter is preferably not more than 10 mass %, more preferably not more than 5 mass %, and still more preferably not more than 1 mass %, relative to a total amount of the particulate hydrogel.

In the present invention, the polymerization step and gel-crushing step can be carried out by any of the following methods: kneader polymerization method of carrying out gel-crushing of a water-containing gel-like crosslinked polymer obtained during the polymerization; and a method of subjecting a water-containing gel-like crosslinked polymer obtained by the continuous belt polymerization to the gel-crushing step.

(2-4) Drying Step

The present step is a step of drying a hydrogel obtained through the polymerization step, etc. to obtain dried polymer. In a case where the aqueous polymerization is carried out in the polymerization step, a hydrogel is gel-crushed (grain-refined) before and/or after dried. Further, the dried polymer (aggregates) obtained by the drying step may be supplied directly to the pulverization step.

A drying method employed in the present step is not particularly limited and can therefore be a variety of methods. Specifically, as the drying method, drying by heating, hot-air drying, drying under reduced pressure, infrared drying, microwave drying, azeotropic dehydration with a hydrophobic organic solvent, high humidity drying with use of high-temperature vapor, and the like method can be used solely or two or more of these methods can be used in combination. A drying temperature is preferably in a range of 100° C. to 300° C., and more preferably in a range of 150° C. to 250° C.

Further, a drying time is not particularly limited because it depends on the surface area of and the moisture content in the hydrogel, the type of drying apparatus, and the like. For example, the drying time is preferably in a range of 1 minute to 5 hours, and more preferably in a range of 5 minutes to 1 hour. Further, a resin solid content is preferably not less than 80 mass %, more preferably in a range of 85 mass % to 99 mass %, and still more preferably in a range of 90 mass % to 98 mass %, where the resin solid content is calculated from weight loss caused by drying (change in mass of 1 g of powder or particles before and after drying at 180° C. for 3 hours).

(2-5) Pulverization Step, Classification Step

The present step is a step of pulverizing and/or classifying a dried polymer obtained in the drying step and is preferably a step of obtaining a water absorbent resin powder having a specific particle size. It should be noted that the present step is different from the above (2-3) gel-crushing step in that a product to be pulverized has undergone the drying step. Further, a water absorbent resin obtained after the pulverization step may be referred to as a "pulverized resin".

(Particle Size Distribution)

The mass average particle diameter (D50) of a water absorbent resin powder before surface-crosslinked is preferably in a range of 200 μm to 600 μm, more preferably in a range of 200 μm to 550 μm, still more preferably in a range of 250 μm to 500 μm, and particularly preferably in a range of 350 μm to 450 μm, from the viewpoint of water absorbing speed, liquid permeability, absorption capacity under load, etc. of a resultant water absorbent resin. Further, the fewer fine particles having a particle diameter of less than 150 μm defined by standard sieve classification, the better. The fine particle content is preferably in a range of 0 mass % to 5 mass %, more preferably in a range of 0 mass % to 3 mass %, and still more preferably in a range of 0 mass % to 1 mass %, from the viewpoint of liquid permeability, etc. of a resultant water absorbent resin.

Still further, the fewer coarse particles having a particle diameter of not less than 850 μm defined by standard sieve classification, the better. The coarse particle content is preferably in a range of 0 mass % to 5 mass %, more preferably in a range of 0 mass % to 3 mass %, and still more preferably in a range of 0 mass % to 1 mass %, from the viewpoint of water absorbing speed, etc. of a resultant water absorbent resin. Yet further, the amount of large particles having a particle diameter of not less than 710 μm is preferably in a range of 0 mass % to 20 mass %, more preferably in a range of 0 mass % to 10 mass %, still more preferably in a range of 0 mass % to 5 mass %, further still more preferably in a range of 0 mass % to 3 mass %, and particularly preferably in a range of 0 mass % to 1 mass %.

Moreover, as to a particle diameter distribution range, particles having particle diameters of preferably not less than 150 μm but less than 850 μm, more preferably not less than 150 μm but less than 710 μm, are preferably contained in an amount of not less than 95 mass %, more preferably in an amount of not less than 98 mass %, and still more preferably in an amount of not less than 99 mass % (upper limit is 100 mass %), from the viewpoint of water absorbing speed, liquid permeability, absorption capacity under load, etc. of a resultant water absorbent resin.

Controlling the mass average particle diameter or the particle diameter (hereinafter also referred to simply as "particle size") of a water absorbent resin powder can be performed in the polymerization step, the gel-crushing step, or the pulverization/classification step after the drying step. Especially, such control is preferably performed in the classification step after the drying. Further, the measurement of the particle size is carried out with use of JIS standard sieves (Z8801-1 (2000)) in accordance with the method defined in International Publication No. WO 2004/69915 or EDANA-ERT420.2-02.

The water absorbent resin powder in accordance with the present invention may be in the form of spheres, in the form of aggregate of the spheres, or in the form of irregular fragments obtained through the pulverization step subjected to the hydrogel or the dried polymer. However, from the viewpoint of water absorbing speed of a resultant water absorbent resin, it is preferable that the water absorbent resin powder is in the form of irregular fragments or in granulated form of the irregular fragments.

In order to further attain the object of the present invention, the particle size is applied preferably to a particle size after the surface crosslinking, and further preferably to the water absorbing agent, which is the final product.

(2-6) Fine Powder Recycling Step

The production method in accordance with the present invention preferably includes, after the drying step, the classification step (including the second classification step performed after the surface crosslinking step; hereinafter the same applies to the following descriptions) of separating a water absorbent resin fine particle passing through a standard sieve having a mesh size of 150 μm, after which the water absorbent resin fine particle or a mixture thereof with water is recycled (reused) in the steps which are performed before the drying step. It should be noted that the coarse particles removed in the classification step may be re-pulverized if necessary. Moreover, the fine particles removed in the classification step may be discarded, used for another purposes, or provided for use in the fine powder recycling step.

Removing the fine particles makes it possible to improve liquid permeability (for example, SFC) of a resultant water absorbent resin. Further, the present step makes it possible to further improve water absorbing speed (for example, FSR).

That is, in the production method in accordance with the present invention, the fine powder recycling step refers to a step of recycling water absorbent resin fine particles (containing, in particular, particles having a particle diameter of not more than 150 μm in amount of not less than 70 mass %; hereinafter also referred to as "fine powder"), which are generated in the drying step, and if necessary, in the pulverization step and in the classification step and then separated out, in such a manner that the fine powder is directly recycled or recycled in the hydrated or granulated form in any of the steps before the drying step, preferably in the polymerization step, the gel-crushing step, or the drying step.

By recycling the fine powder, it is possible to control particle sizes of a water absorbent resin and a water absorbing agent and to further improve the water absorbing speed of a water absorbent resin obtained by the present step.

The fine powder to be recycled may be a fine powder before or after the surface crosslinking. The amount of the recycled fine powder is preferably in a range of 1 mass % to 40 mass %, and more preferably in a range of 5 mass % to 30 mass % relative to the total mass of dried polymer.

A preferable fine powder recycling method in the present invention is a method in which the water absorbent resin fine particle or a product in hydrated or granulated form of the water absorbent resin fine particle, and if necessary, inorganic fine particles and others are mixed into the monomer aqueous solution to be polymerized, the hydrogel during the polymerization, or a drying machine used in the drying step. A method of recycling the fine powder into the monomer aqueous solution to be polymerized is exemplified by the methods disclosed in PCT international publications Nos. 92/001008 and 92/020723. A method of recycling the fine powder into the hydrogel during the polymerization is exemplified by the methods disclosed in PCT international publications Nos. 2007/074167, 2009/109563, 2009/153196, and 2010/006937. Further, a method of performing recycling in the drying step (into a drying machine) is exemplified by the method disclosed in U.S. Pat. No. 6,228,930, etc. These fine powder recycling methods can be adopted suitably as the fine powder recycling method in the present invention.

(2-7) Surface Crosslinking Agent Addition Step

The present step is a step of preparing a water absorbent resin powder containing a surface crosslinking agent provided in the surface crosslinking step. In common practice, surface crosslinking is carried out, for example, by adding an organic surface crosslinking agent described later, by polymerizing the monomer(s) on a surface of a water absorbent resin powder, by adding a radical polymerization initiator such as persulfate and then by heating or ultraviolet irradiation, or the like. In the surface crosslinking agent addition step of the present invention, it is preferable that the organic surface crosslinking agent is added to the water absorbent resin powder obtained in the above classification step and further to a water absorbent resin powder obtained in the fine powder recycling step. Further, surface crosslinking may be carried out simultaneously with a liquid permeability enhancer addition step described later. Note that the organic surface crosslinking agent is a crosslinking agent that cross-links with a functional group of a water absorbent resin, especially a carboxyl group of the water absorbent resin, by a covalent bond or a dehydration reaction. As an organic surface crosslinking agent, a polymer organic crosslinking agent or a non-polymer organic crosslinking agent, preferably a non-polymer organic crosslinking agent, more preferably a non-polymer organic crosslinking agent having a molecular weight of 60 to 1000 is used. The non-polymer organic crosslinking agent is preferably a water-soluble organic crosslinking agent (having a solubility of preferably not less than 1 g, more preferably not less than 5 g, particularly preferably not less than 10 g in 100 g of water at 25° C.). Note that low molecular polyethylene glycol (for example, di, tri, tetra, and penta) having a weight average amount of not more than 1000 is classified as non-polymer one.

(Organic Surface Crosslinking Agent)

Examples of the organic surface crosslinking agent usable in the present invention encompass polyhydric alcohol compounds, epoxy compounds, polyhydric amine compounds, condensates of a polyhydric amine compound and a haloepoxy compound, oxazoline compounds, (mono)oxazolidinone compounds, (di)oxazolidinone compounds, (poly)oxazolidinone compounds, oxetane compounds, alkylene carbonate compounds, and the like, from the viewpoint of physical properties of a resultant water absorbent resin powder. Among them, it is particularly preferable to employ a dehydration reaction crosslinking agent including any of a polyhydric alcohol compound, an alkylene carbonate compound, an oxazolidinone compound, and the like, which require high-temperature dehydration reaction.

The dehydration reaction surface crosslinking agent is a surface crosslinking agent causing dehydrative esterification reaction of a carboxyl group, which is a functional group of a polyacrylic acid (salt)-based water absorbent resin powder, with a hydroxyl group, which is a functional group of the surface crosslinking agent, or causing dehydrative amidation reaction of the carboxyl group with an amino group, which is a functional group of the surface crosslinking agent. Cyclic surface crosslinking agents, like the alkylene carbonate compounds and the oxazolidinone compounds, with which a hydroxyl group and an amino group are generated in the process of the reaction are also classified as the dehydration reaction surface crosslinking agent.

Although a polymer or non-polymer polyhydric amine compound is also a dehydration reaction crosslinking agent having an amino group, an amino group in a polyhydric amine compound generally has an extremely high reaction temperature required for dehydration reaction, and Is prone to deterioration and coloring as a result of high-temperature heating. Therefore, a polyhydric amine compound is classified and used as an ion reactive crosslinking agent or as a liquid permeability enhancer to be used at a usual temperature when the surface crosslinking agent addition step is carried out. On the other hand, in a case where an epoxy group is introduced (epoxy modifying, particularly glycidyl modifying) in a polyhydric amine compound, the polyhydric amine compound has a low-temperature reactivity, and is therefore classified and used as an organic surface crosslinking agent to be used.

Specific examples of the organic surface crosslinking agent encompass: polyalcohol compounds such as (di)ethylene glycol, (tri)ethylene glycol, (tetra)ethylene glycol, (poly)ethylene glycol, (di)propylene glycol, (poly)propylene glycol, 1,3-propanediol, 2,2,4-trimethyl-1,3-pentanediol, (poly)glycerin, 2-butene-1,4-diol, 1,4-butanediol, 1,3-butanediol, 1,5-pentanediol, 1,6-hexanediol, trimethylolpropane, diethanolamine, triethanolamine, pentaerythritol, and sorbitol; epoxy compounds such as (poly)ethylene glycol diglycidyl ether, (di)glycerol polyglycidyl ether, (poly)glycerol polyglycidyl ether, and glycidol; oxazoline compounds such as 2-oxazolidone, N-hydroxyethyl-2-oxazolidone, and 1,2-ethylene bisoxazoline; alkylene carbonate compounds such as 1,3-dioxolane-2-one, 4-methyl-1,3-dioxolane-2-one, 4,5-dimethyl-1,3-dioxolane-2-one, 4,4-dimethyl-1,3-dioxolane-2-one, 4-ethyl-1,3-dioxolane-2-one, 4-hydroxymethyl-1,3-dioxolane-2-one, 1,3-dioxane-2-one, 4-methyl-1,3-dioxane-2-one, 4,6-dimethyl-1,3-dioxane-2-one, and 1,3-dioxopane-2-one; haloepoxy compounds such as epichlorohydrin, epibromohydrin and α-methylepichlorohydrin and polyhydric amine adducts thereof (epoxy-modified polyvalent amine polymer, for example, Kymene® manufactured by Hercules); silane coupling agents such as γ-glycidoxypropyltrimethoxysilane and γ-aminopropyltriethoxysilane; oxetane compounds such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, 3-butyl-3-oxetane ethanol, 3-chloromethyl-3-methyloxetane, 3-chloromethyl-3-ethyloxetane, and polyhydric oxetane compounds; cyclic urea compounds such as 2-imidazolidinone; and the like.

Among these, the organic surface crosslinking agent is preferably selected from the polyhydric alcohol compounds, the epoxy compounds, the oxazoline compounds, and the alkylene carbonate compounds. More preferably, the organic surface crosslinking agent is a combination of any compound selected from the polyhydric alcohol compounds and any compound selected from organic surface crosslinking agents (epoxy compounds, oxazolinone compounds, and the alkylene carbonate compounds) other than polyhydric alcohols.

From the viewpoint of higher physical properties of a resultant water absorbent resin powder, it is preferable that the organic surface crosslinking agent is a combination of particularly a polyhydric alcohol and a compound (preferably, an epoxy compound or an alkylene carbonate, and particularly preferably, an alkylene carbonate) other than the polyhydric alcohols. As a suitable surface crosslinking method, any of the methods described in the pamphlet of International Publication No. WO 2012/102406 and the pamphlet of International Publication No. WO 2012/102407 is employed.

The organic surface crosslinking agent is preferably a combination of a plurality compounds selected from the polyhydric alcohols, the alkylene carbonates, the oxazolidinone compounds, the oxetane compounds, and amino alcohol compounds, more preferably a combination of particularly the polyhydric alcohols and cyclic compounds selected from the alkylene carbonates, the oxazolidinone compounds, and the oxetane compounds, and still more preferably a combination of any polyhydric alcohol and any alkylene carbonate as described in the above two pamphlets of International Publication. Particularly preferably, any of the methods described in (2-8), (2-9), and (3-3) to (3-9) of the above two pamphlets of International Publication is employed as the surface crosslinking agent addition step of the present invention, and these descriptions shall be descriptions of the present application.

The polyhydric alcohols are C2-C8 polyhydric alcohols, preferably C3-C6 polyhydric alcohols, and particularly preferably C3 or C4 polyhydric alcohols. Specifically, the polyhydric alcohols are preferably, for example, diols, and examples of the diols encompass ethylene glycol, propylene glycol, and 1,3-propanediol, 1,4-butanediol.

In a case where the dehydration reaction surface crosslinking agent is a combination of any of the polyhydric alcohols and any surface crosslinking agent other than the polyhydric alcohols, a ratio (mass ratio) of any of the polyhydric alcohols to any surface crosslinking agent other than the polyhydric alcohols is typically 1:9 to 9:1, preferably 2:8 to 8:2, more preferably 3:7 to 7:3, and particularly preferably 5:5 to 7:3, wherein the ratio is a ratio of the mass of the polyhydric alcohol to the total mass of the material other than the polyhydric alcohol in the dehydration reaction surface crosslinking agent. The material other than the polyhydric alcohol in the dehydration reaction surface crosslinking agent is preferably the cyclic compound, more preferably an alkylene carbonate, and still more preferably an ethylene carbonate.

The polyhydric alcohol compound as used in the present invention is suitably propylene glycol, 1,3-propanediol, and 1,4-butanediol. Further, the epoxy compound as used in the present invention is suitably a polyglycidyl compound. The oxazoline compound as used in the present invention is suitably 2-oxazolidinone, and the alkylene carbonate compound as used in the present invention is suitably 1,3-dioxolane-2-one.

A temperature of a solvent to be mixed into the organic surface crosslinking agent is appropriately determined. A solvent being too low in temperature may result in too low solubility and too high viscosity. Especially, in a case where a solid non-polymerized organic compound described later is used as the surface crosslinking agent, particularly, ethylene carbonate is used as the surface crosslinking agent, it is preferable that the solvent as used is water warmed to room temperature or higher (preferably in a range of 30° C. to 100° C., more preferably in a range of 35° C. to 70° C., and still more preferably in a range of 40° C. to 65° C.).

That is, it is preferable that other compound, water in particular, to be mixed with a non-polymerized organic compound (particularly, a solid surface crosslinking agent, and further, a solid polyhydric alcohol and a solid cyclic compound such as alkylene carbonate) is warmed, and it is more preferable that the other compound is in the aforementioned temperature range.

The alkylene carbonate compound or the polyhydric alcohol compound, particularly a solid alkylene carbonate compound, is preferably heated in advance before mixture with water. A temperature of the compound thus heated is preferably a temperature higher than the temperature of a surface crosslinking agent solution having water added thereto. Specifically, in a case where the solid alkylene carbonate compound is used, it is preferable that the polyhydric alcohol, particularly the solid polyhydric alcohol is also heated and melted to a temperature preferably in a range of 30° C. to 100° C., more preferably in a range of 35° C. to 70° C., and still more preferably in a range of 40° C. to 65° C.

(Mixture Ratio Control)

A mixture control ratio of the surface crosslinking agent solution in the present invention depends on subtle variation in concentration and ratio of the surface crosslinking agent solution. Particularly, the subtle variation in concentration and ratio of the surface crosslinking agent solution may occur due to air temperature changes every day or every season. For this reason, it is preferable that the mixture of the surface crosslinking agent solution in the present invention into a water absorbent resin powder is performed while a flow rate is measured with a mass flowmeter, particularly Coriolis-type mass flowmeter.

When a moving mass encounters vibration vertical to a moving direction, a Coriolis force in response to a velocity of the mass is generated. The Coriolis mass flowmeter is provided with a resonating, measuring tube for correctly generating this effect, and when a fluid (=mass) moves in the measuring tube, a Coriolis force is generated. By sensors at an outlet and an inlet, slippage of a vibration phase of a measuring tube is sensed, and a microprocessor analyzes and uses this information to calculate a mass flow rate. Further, by a resonating frequency of the measuring tube, direct measurement of a fluid density is possible, and a temperature of the measuring tube is also measured for correcting influence of a temperature. This signal corresponds to a temperature of a process, and can be also used as an output signal. The Coriolis-type mass flowmeter is suitably used not only in preparation of a surface crosslinking agent at a predetermined ratio, but also in mixture of a surface crosslinking agent into a water absorbent resin after the preparation.

(Solvent and Concentration)

In a case where the organic surface crosslinking agent is used, the organic surface crosslinking agent is used preferably in an amount (total amount throughout the addition step) of 0.001 parts by mass to 15 parts by mass, and more preferably 0.01 parts by mass to 5 parts by mass, relative to 100 parts by mass of the water absorbent resin before the addition of the organic surface crosslinking agent.

In a case where the organic surface crosslinking agent as used is two types of compounds, i.e. a polyhydric alcohol compound and a compound selected from among compounds other than polyhydric alcohol compounds, the polyhydric alcohol compound is used preferably in an amount (total amount throughout the addition step) of 0.001 parts by mass to 10 parts by mass, and more preferably 0.01 parts by mass to 5 parts by mass, relative to 100 parts by mass of the water absorbent resin before the addition of the organic surface crosslinking agent. Further, the compound other than the polyhydric alcohol compound is used in an amount (total amount throughout the addition step) of 0.001 parts by mass to 10 parts by mass, and more preferably 0.01 parts by mass to 5 parts by mass relative to 100 parts by mass of the water absorbent resin before the addition of the organic surface crosslinking agent.

The surface crosslinking agent solution preferably contains water. That is, it is preferable that the surface crosslinking agent solution is an aqueous surface crosslinking agent solution. The water is used preferably in an amount (total amount throughout the addition step) of 0.5 parts by mass to 20 parts by mass, and more preferably 0.5 parts by mass to 10 parts by mass, relative to 100 parts by mass of the water absorbent resin before the addition of the organic surface crosslinking agent. It should be noted that the water also includes crystalline water, hydrated water, or the like of the surface crosslinking agent.

Further, a hydrophilic organic solvent may be used in the surface crosslinking agent addition step. The hydrophilic organic solvent is used preferably in an amount of more than 0 part by mass but not more than 10 parts by mass, more preferably in an amount of more than 0 part by mass but not more than 5 parts by mass, relative to 100 parts by mass of the water absorbent resin before the addition step. Examples of the hydrophilic organic solvent encompass a $C_1$-$C_4$ primary alcohol, a $C_2$-$C_3$ primary alcohol, lower ketones whose carbon number is 4 or lower, such as acetone, and the like. In particular, volatile alcohols each having a boiling point of lower than 150° C., more preferably lower than 100° C., are more preferable as the hydrophilic organic solvent, because the volatile alcohols evaporate during the surface crosslinking and therefore no residue will remain.

Specifically, examples of the hydrophilic organic solvent encompass: lower alcohols such as methyl alcohol, ethyl alcohol, n-propyl alcohol, isopropyl alcohol, n-butyl alcohol, isobutyl alcohol, and t-butyl alcohol; ketones such as acetone; ethers such as dioxane, tetrahydrofuran, and methoxy (poly)ethylene glycol; amides such as epsilon-caprolactam and N,N-dimethylformamide; sulfoxides such as dimethyl sulfoxide; polyhydric alcohols such as polyoxypropylene and oxyethylene-oxypropylene block copolymers; and the like.

Further, in mixing a surface crosslinking agent solution into a water absorbent resin powder, water-insoluble fine particles and a surfactant may be added in an amount within a range such that the effect of the present invention is not interfered with. Specifically, the water-insoluble fine particles and the surfactant can coexist in an amount of more than 0 part by mass but not more than 10 parts by mass, preferably more than 0 part by mass but not more than 5 parts by mass, and more preferably more than 0 part by mass but not more than 1 part by mass, relative to 100 parts by mass of a water absorbent resin before the addition step. In this case, a surfactant or the like as used in the present invention can be the one disclosed in U.S. Pat. No. 7,473,739, etc.

A concentration of a surface crosslinking agent in the surface crosslinking agent solution is appropriately determined. The surface crosslinking agent solutions in the present invention can be aqueous surface crosslinking agent solutions such that the surface crosslinking agent concentration based on a total amount of all of the surface crosslinking agents in the individual surface crosslinking agent solutions used in all of the addition processes, is in a range of 1 mass % to 80 mass % and is further in a range of 5 mass % to 60 mass %, in a range of 10 mass % to 40 mass %, or in a range of 15 mass % to 30 mass %. It should be noted that the hydrophilic organic solvent and/or other component(s) may be contained as a residue.

A temperature of the surface crosslinking agent solution is appropriately determined based on solubility of a surface crosslinking agent to be used, viscosity of the surface crosslinking agent solution, or the like. The temperature of the surface crosslinking agent solution is preferably in a range of −10° C. to 100° C., more preferably in a range of 5° C. to 70° C., still more preferably in a range of 10° C. to 65° C., and particularly preferably in a range of 25° C. to 50° C. The surface crosslinking agent solution having a high temperature is not preferable because it can cause, before mixed or reacted with a water absorbent resin powder, the followings: (1) In a case where the surface crosslinking agent is a cyclic surface crosslinking agent, the cyclic surface crosslinking agent is hydrolyzed (e.g. degradation from ethylene carbonate into ethylene glycol, degradation from oxazolidinone into ethanolamine); and (2) mixability is deteriorated by volatilization and the like of water and a hydrophilic organic solvent contained in the surface crosslinking agent solution. The surface crosslinking agent solution having a low temperature may cause (1) coagulation of the surface crosslinking agent solution and (2) precipitation of the surface crosslinking agent.

(Surfactant)

A polyacrylic acid (salt)-based water absorbent resin powder of the present invention may contain a surfactant, and it is preferable that a surfactant is mixed in any of the steps included in the production method according to the present invention.

By coating the surface of the water absorbent resin powder in the present invention with a surfactant, it is possible to obtain a water absorbent resin powder having a high water absorbing speed and a high liquid permeability. It should be noted that the surfactant used in the present invention is not particularly limited, but examples of the surfactant encompass surfactants disclosed in International Publication No. WO 97/017397 and U.S. Pat. No. 6,107,358, i.e. nonionic surfactants, anionic surfactants, cationic surfactants, amphoteric surfactants, and the like. These surfactants may have polymerizability or reactivity with an acrylic acid (salt)-based monomer or a water absorbent resin powder. As a specific compound for the surfactant, compounds described in (2-1) of Patent Literatures 45 and 46 are employed.

The type and use amount of a surfactant to be used is determined appropriately. The surfactant in the present invention is used preferably in a range such that the surface tension described in U.S. Patent No. 2006/204755 is obtained. Specifically, the use amount of the surfactant in the present invention is in a range of 0 part by weight to 0.5 parts by weight, in a range of 0.00001 parts by weight to 0.1 parts by weight, or in a range of 0.001 parts by weight to 0.05 parts by weight, relative to a water absorbent resin. Among the aforementioned surfactants, anionic surfactants, nonionic surfactants, or silicone surfactants are preferably used. More preferably, nonionic surfactants or silicone surfactants are used.

(Use of a Surface Crosslinking Agent Solution in Combination with an Acid or a Base)

For the purpose of promoting reaction and uniform mixture of a surface crosslinking agent, the surface crosslinking agent solution may contain not only the organic surface crosslinking agent, the hydrophilic organic solvent, the surfactant, and water-insoluble fine particles, but also an acid or a base.

As the acid or the base, an organic acid or a salt thereof, an inorganic acid or a salt thereof, and an inorganic base can be used. The acid or the base is appropriately used in an amount in a range of 0 part by mass to 10 parts by mass, more preferably in a range of 0.001 parts by mass to 5 parts by mass, and still more preferably in a range of 0.01 parts by mass to 3 parts by mass, relative to 100 parts by mass of the water absorbent resin before added with the surface crosslinking agent solution. The organic acid is a $C_1$-$C_6$, more preferably a $C_2$-$C_4$, water-soluble organic acid, water-soluble saturated organic acid, and saturated organic acid containing a hydroxyl group, and particularly preferably a saturated organic acid containing a hydroxyl group.

Another examples of the acid or the base encompass; non-crosslinkable, water-soluble inorganic bases (preferably, an alkali metal salt, an ammonium salt, a hydroxide of an alkali metal, and an ammonia or a hydroxide thereof); an irreducible-alkali-metal-salt pH buffer (preferably bicarbonate, dihydrogen phosphate, hydrogen phosphate etc.); and the like.

(Method by which to Add a Surface Crosslinking Agent Solution)

By an addition process, the surface crosslinking agent is added to a water absorbent resin powder. Examples of a method for the addition process, which is not particularly limited, include: (1) a method of immersing a water absorbent resin into a hydrophilic organic solvent so as to cause a surface crosslinking agent to be adsorbed to the water absorbent resin; (2) a method of spraying or dropping a surface crosslinking agent solution directly to a water absorbent resin so as to mix the water absorbent resin with the surface crosslinking agent solution; and the like. From the viewpoint of evenly adding a predetermined amount of surface crosslinking agent to a water absorbent resin, the method (2) is preferable. Further, it is preferable that the addition process is performed while the water absorbent resin is stirred in order that the surface crosslinking agent is evenly added to the water absorbent resin. Spraying the surface crosslinking agent is more preferable.

In a case where two or more types of surface crosslinking agents having mutually different compositions are used in the addition process, different spray nozzles, for example, may be used for simultaneous addition of the surface crosslinking agents. However, from the viewpoint of evenly adding the surface crosslinking agents, it is preferable that before the addition, these surface crosslinking agents are adjusted into a surface crosslinking agent having a single composition. Further, in a case where the surface crosslinking agent has a single composition, a plurality of spray nozzles may be used in consideration of size and throughput of an apparatus to be used in the addition process, spraying angle of a spray nozzle, and others.

Preferable examples of an apparatus for use in the addition process (hereinafter also referred to as "mixing apparatus") encompass, cylindrical mixers, double-wall conical mixers, V-shaped mixers, ribbon mixers, screw type mixers, fluidization type furnaces, rotary disc mixers, air mixtures, double-arm kneaders, internal mixers, pulverizing type kneaders, rotating mixers, screw-type extruders, Turbulizer, ploughshare mixers, and the like. Further, in large-scale production such as commercial production, the mixing apparatus is preferably an apparatus capable of performing continuous mixture. Still further, one and the same apparatus may be used in each of the addition processes, or separate apparatuses may be used in the addition processes.

The water absorbent resin powder used in the present step is preferably heated and warmed. The temperature of the water absorbent resin powder is preferably in a range of 30° C. to 100° C., more preferably in a range of 35° C. to 80° C., and still more preferably in a range of 40° C. to 70° C. A water absorbent resin powder having a low temperature causes precipitation of a surface crosslinking agent, moisture adsorption of a water absorbent resin, or the like, which may result in inadequate or uneven surface treatment or the like to the water absorbent resin powder. A water absorbent resin powder having an extremely high temperature, particularly a temperature higher than a boiling point of water in a case where a surface crosslinking agent solution is an aqueous surface crosslinking agent solution, causes evaporation or the like of water contained in the aqueous surface crosslinking agent solution, which may in turn precipitation or the like of the surface crosslinking agent. The temperature of a mixture obtained through the present step, i.e. a mixture of the surface crosslinking agent solution and a water absorbent resin powder, is preferably in a range of 30° C. to 100° C., more preferably in a range of 30° C. to 90° C., and still more preferably in a range of 30° C. to 80° C.

The mixture having a temperature falling within the above range yields the following effect: an added surface crosslinking agent can be effectively reacted in the surface crosslinking step described later and also keep an appropriate fluidity.

(2-8) Surface Crosslinking Step

The present step is a step of performing heat treatment for crosslinking the surface of the water absorbent resin powder or the periphery of the surface of the water absorbent resin powder, in order to improve absorption capacity under load and liquid permeability of a water absorbent resin powder. The present step can be carried out simultaneously with the surface crosslinking agent addition step or after the surface crosslinking agent addition step. The present step is preferably carried out after the surface crosslinking agent addition step, from the viewpoint of quality stabilization. In a production method according to the present invention, the present step may be carried out once or may be carried out twice or more times under one and the same condition or under different conditions. It should be, however, noted that it is possible to obtain a water absorbing agent according to the present invention by performing the present step at least once under an atmosphere controlled at a specific dew point.

(Heating Apparatus)

A heating apparatus as used in the present invention is exemplified by a continuous type or batch type heating apparatus including (a) a publicly known drier or a publicly known heating furnace and (b) a gas discharge mechanism and/or a gas supply mechanism for causing the drier or the heating furnace to have a predetermined atmosphere. The continuous type heating apparatus is preferable.

A heating method of the heating apparatus is suitably a method of a conductive heat transfer type, a method of a radiative heat transfer type, a method of a hot-air heat transfer type, a method of a dielectric heating type. The heating method is preferably the heating method of a conductive heat transfer type and/or of a hot-air heat transfer type, and more preferably the heating method of a conductive heat transfer type.

A control temperature of the heating apparatus needs only to be a temperature at which a water absorbent resin can be heated to a temperature described later, and needs not to be held constant from the beginning to the end of the surface crosslinking step. In order to prevent partial overheating and the like, the temperature of the heating apparatus is preferably in a range of 100° C. to 300° C., more preferably in a range of 120° C. to 280° C., still more preferably in a range of 150° C. to 250° C., and particularly preferably in a range of 170° C. to 230° C. during not less than 70%, particularly not less than 90%, and substantially an entire period of time from the beginning to the end of the surface crosslinking step.

Further, in order to enhance the efficiency of heating and perform an even heat treatment, it is preferable to use an apparatus including a mechanism for continuously stirring and/or fluidizing an object to be heated. A stirring and/or a fluidizing method is preferably a channel stirring method, a method of a screw type, a method of a rotary type, a method of a disc type, a method of a kneading type, a method of a fluidized-bed type, and the like. It is more preferable that a stirring method using stirring blades (paddles) and a stirring method based on movement of a heat transfer surface itself by means of a rotary retort furnace. It should be noted that the stirring and/or fluidizing mechanism used for the purpose of performing an even heat treatment need not to be used in a case where the amount of product to be dried is small, for example, in a case where an object to be dried has a thickness of less than 1 cm.

The heating apparatus includes the gas discharge mechanism for discharging vapors generated from an object to be heated and also is able to control atmospheric dew point and temperature of a heating section (the inside of the heating apparatus) by adjusting the gas discharge mechanism, for example, by adjusting the amount of discharge. It should be noted that the heating section is not the so-called heat source such as a heater or an induction coil but a place to increase the temperature of the object to be heated.

The discharge mechanism corresponds to an air exit. If gas is discharged from an outlet of a heated product, the outlet also corresponds to the discharge mechanism. Further, it is preferable the discharge mechanism adjusts the amount of gas discharged therefrom and a pressure of the gas discharged therefrom by means of a blower or the like. Still further, an air exit in the heating apparatus is not limited to one air exit. A plurality of air exit points can be provided in consideration of the size of the heating apparatus and an adjustment status of the dew point and temperature.

The heating apparatus includes the gas supply mechanism and also is able to control an atmospheric dew point and an atmospheric temperature in the heating section by adjusting the gas supply mechanism, for example, by adjusting the amount of supply.

The adjustment in atmospheric temperature can be carried out by using a part of a heating area of the heating section of the heating apparatus, in which part a water absorbent resin as an object to be heated is not provided. In this case, it is possible to increase the efficiency of heating of gas (gas to be supplied) by using a filler such as a metallic ring-shaped object, a metallic mesh-shaped object, a ceramic ring-shaped object, or a ceramic mesh-shaped object.

In terms of stability of the atmospheric temperature and dew point described below, it is preferable that a direction of airflow in the heating section is controlled to be a constant direction. Particularly, in a case where an apparatus capable of continuous processing is used, the airflow is preferably plumb or horizontal with respect to a flow from an input port of an object to be heated toward an output port, more preferably horizontal, still more preferably a counter-current flow and/or a concurrent flow, and particularly preferably a concurrent flow. It should be noted that the term "a given direction" means that a direction of a flow of a substance does not change from a macroscopic viewpoint rather than one and the same direction in every point. For example, a partial and/or temporary turbulent or vortex state of airflow by stirring, etc. is not subject to the control of airflow in the present invention. On the other hand, a state in which gas is drawn from the input port and gas is discharged from the output port is turned in the middle of the heat treatment into a state in which gas is drawn from the output port and is discharged from the input port, such a change can be expressed as being "not a constant direction."

In a case where a large-size heating apparatus includes a plurality of gas discharge ports and a plurality of gas supply ports, particularly in a case where a continuous processing type heating apparatus is used, for example, a point of concurrent flow and a point of counter-current flow may coexist in the heating section, provided that the direction of the airflow does not change over time at the individual points.

Since a flow rate of the airflow varies depending on a size of an apparatus particularly in continuous production, the flow rate is not particularly limited, provided that the flow rate can control the atmospheric temperature and dew point inside the apparatus to fall within a predetermined range. However, the flow rate is preferably at least more than 0 $Nm^3$/hr but not more than 10000 $Nm^3$/hr, more preferably at least more than 0 $Nm^3$/hr but not more than 5000 $Nm^3$/hr, and still more preferably at least more than 0 $Nm^3$/hr but not more than 3000 $Nm^3$/hr. Further, a ratio of gas relative to the amount of a water absorbent resin powder to be processed is preferably not more than 3000 $Nm^3$/ton, and more preferably not more than 1000 $Nm^3$/ton. It should be noted that "$Nm^3$" indicates a volume of gas obtained by conversion on a standard-state basis (0° C., 1 atmosphere) rather than a volume of gas that exists under a condition of 0° C. and 1 atmosphere.

The flow rate and the ratio are values defined by a total flow rate of gas discharged and the weight of a water absorbent resin, before heat-treated, introduced into the apparatus. It should be noted that the ratio may fall outside in a case where continuous production of the apparatus is not in a steady state, such as at the start of an operation of the apparatus and at the end of the operation of the apparatus.

The gas to be supplied can be air, an inert gas such as a nitrogen gas, or a mixture of these with water vapor, provided that a dew point can be controlled to be constant. The gas to be supplied may be appropriately reduced or pressurized and may be appropriately heated or cooled. Usually, the gas to be supplied needs only to be supplied under a condition where an air having a temperature around room temperature (e.g. 0° C. to 50° C.) is under substantially atmospheric pressure (101.3 kPa (1 atmosphere) ±10%, preferably ±5%, more preferably ±1%).

It is preferable that a pressure of gas in the heating section is slightly lower than a normal atmospheric pressure (101.3 kPa (1 atmosphere)). Such a pressure differential is preferably in a range of 0 kPa to −10 kPa, more preferably in a range of 0 kPa to −5 kPa, and still more preferably in a range of 0 kPa to −2 kPa, relative to atmospheric pressure.

In making industrial continuous production, it is possible to use a batch processing-type or continuous processing-type heating apparatus including the above mechanism.

In the case of the batch type heating apparatus, a method of standing an object to be heated in one or more trays or the like in a manner so as to be distributed substantially evenly, a method of filling an object to be heated in a single bath or a plurality of baths and then heating the object to be heated while stirring with stirring blades or the like, a method of filling an object to be heated in a fluidized bed and then heating the object to be heated while stirring with stirring blades or the like, or the like method is used. In the case of the continuous processing type heating apparatus, a method of carrying a belt or a plurality of trays on which an object to be heated is distributed substantially evenly, a method of carrying an object to be heated while stirring with stirring blades, a screw, or the like, a method of carrying an object to be heated by an inclined heating surface, or the like is used.

Specifically, a heating apparatus used in the present invention is preferably a conductive heat transfer type heating apparatus including a continuous stirring mechanism using pressurized steam (high pressure steam) as a heat source. Further, in order to efficiently perform continuous production, a heating apparatus used in the present invention preferably has a slope (tilted at an angle of more than 0 degree relative to a horizontal plane) by which an object to be heated can be flown down to the output port by gravity flow. If the tilt angle of the slope pointing downward is too large, it may cause variations in heating time. For this reason, the slope of the heating apparatus has a tilt angle of preferably in a range of more than 0 degree to not more than 20 degrees and more preferably in a range of more than 0 degree to not more than 10 degrees, relative to the horizontal plane.

It should be noted that in a case where the addition process is performed before the heat treatment and after the heat treatment, one and the same apparatus as used in the above addition process may be used in these addition processes. Alternatively, separate apparatuses may be used in these addition processes. Particularly, in a case where a production apparatus of continuous type is used, it is preferable in terms of production efficiency that one and the same apparatus is used both in the addition process performed before heating and the heat treatment while another apparatus is used in the addition process performed after heating.

Further alternatively, a plurality of heating apparatuses may be used, wherein one type of combination of the aforementioned heating schemes, stirring schemes, gas discharge schemes, and gas supply schemes or different types of combinations of these schemes are employed in each of the heating apparatuses.

For the control of an atmospheric dew point and temperature described later, the aforementioned gas discharge amount, temperature of gas to be supplied, flow rate, dew point, etc. are appropriately controlled in consideration of (i) heat transfer from wall surfaces of a heating apparatus or from a water absorbent resin and (ii) rise in dew point due to water vapors generated from a water absorbent resin in a heating apparatus.

(Atmospheric Dew Point and Temperature)

The atmospheric dew point and temperature in the present step means atmospheric dew point and temperature of gas that exists in an upper space above an object to be heated in the heating section of the heating apparatus.

A method of adjusting the dew point is exemplified by a (a) method of using, as the gas to be supplied, steam, dry air, nitrogen, helium, argon, and/or dried air, and a (b) method of using water vapor generated from water contained in a water absorbent resin powder when the a water absorbent resin powder is heated in the present step. A specific method of adjusting the dew point is exemplified by, for example, a method of providing a device for measuring a dew point in the heating apparatus so that the dew point can be adjusted as required with the above gas introduced into the heating apparatus, a method of adjusting the dew point by changing the flow rate and pressure of discharge gas derived from the above gas. In the present invention, a plurality of method may be suitably used in combination if necessary.

The atmospheric dew point is controlled in the range of 45° C. to 100° C., preferably in the range of 50° C. to 98° C., and more preferably in the range of 55° C. to 95° C.

In order to prevent condensation in the heating section, the atmospheric temperature is preferably a temperature of not lower than the dew point. A specific atmospheric temperature is in a range of 100° C. to 300° C., more preferably in a range of 100° C. to 250° C., and still more preferably in a range of 100° C. to 230° C. It should be noted that the dew point is to be set as described above.

The atmospheric dew point and temperature each change depending upon a location inside the heating section and with a lapse of a processing time. However, the atmospheric dew point and temperature are particularly preferably controlled to fall within given ranges in the apparatus (it is preferable that the atmospheric dew point and temperature do not fall outside the above respective ranges and that a range of a variation (difference between an upper limit and a lower limit of the dew point) in atmospheric dew point and temperature falls within 20° C., and the variation range falls more preferably within 10° C., still more preferably within 5° C., and particularly preferably within 2° C.).

The temperature and dew point are values measured under the above atmosphere in an upper space plumb to a water absorbent resin powder being heated in the heating section. In a case where dew points measured in a plumb direction vary depending on an apparatus used, the highest dew point in the dew points is the dew point in the present invention. It should be noted that the dew point can fall outside the aforementioned range during the step of performing heat treatment (for example, immediately after the introduction of the water absorbent resin powder into the heating section and/or immediately before the discharge from the heating section in the continuous processing method). In order to sufficiently obtain the effect of the present invention, it is only necessary that an atmosphere in the heating section is such that the dew point and the temperature reach the above dew point and the above temperature from a point in time when the temperature of a water absorbent resin powder in the heating section, for the first time, reaches 170° C. or higher, more preferably 150° C., still more preferably 130° C., and particularly preferably 100° C. or higher onwards.

It should be noted that if the flow rate of gas falls within the above range, a dew point and temperature at an appropriate measurement point inside the gas discharge mechanism of the heating apparatus may be set as the atmospheric dew point and temperature in the present invention. Specifically, no mixture with other gas occurs midway from the heating section to the measurement point, and no treatment is made by means of a gas cleaning device or the like, a compulsory temperature change processing using a heater, a cooler, etc. Is not performed, and a time between discharge of gas from the heating section and reach to the measurement point is within one second.

The heat treatment in the surface crosslinking step needs only to be such that a maximum temperature of a water absorbent resin powder as an object to be heated in the surface crosslinking step is higher than an atmospheric dew point of a gas. The maximum temperature is preferably in a range of 175° C. to 300° C., more preferably in a range of 175° C. to 250° C., and particularly preferably in a range of 180° C. to 230° C. If the maximum temperature is below 175° C., covalent bonds for surface crosslinking may be formed insufficiently. If the maximum temperature is above 300° C., a resultant water absorbent resin may be deteriorated. A time period of the heat treatment is not particularly limited, provided that the above temperature condition is satisfied. However, the time period of the heat treatment is usually in a range of 1 minute to 120 minutes and preferably in a range of 5 minutes to 60 minutes.

A variation (%) in solid content before and after the surface crosslinking (i.e. difference between a solid content in a water absorbent resin before the surface crosslinking agent addition step (the solid content after drying) and a solid content in a water absorbent resin after the surface crosslinking) can be constant, increased, or decreased. In order to maximize the effects of the present invention, a solid content after the surface crosslinking is preferably lowered, with the use of the dehydration reaction crosslinking agent, (i) than a solid content before the surface crosslinking by not less than 2% or (ii) by less than 2 wt % after the surface crosslinking.

Further, for the purpose of preventing the occurrence of excessive crosslinking reaction and improving handling property in a subsequent step, a water absorbent resin taken out of the heating apparatus may be cooled, as required, to a temperature of preferably lower than 100° C., and more preferably in a range of 0° C. to 95° C., or in a range of 40° C. to 90° C.

(2-9) Step of Adding an Additive

In the production method according to the present invention, it is essential that an additive selected from additives (liquid permeability enhancers), particularly from water-insoluble fine particulate compounds and polyvalent cationic compounds is added. The step of adding an additive selected from the water-insoluble fine particulate compounds and the polyvalent cationic compounds may be carried out simultaneously with the surface crosslinking agent addition step or may be carried out after the surface crosslinking step.

"Carrying out the step of adding an additive simultaneously with the surface crosslinking agent addition step" is any of the following processes: (a) adding the additive which is being mixed into the surface crosslinking agent or the surface crosslinking agent solution; (b) adding the additive simultaneously with the surface crosslinking agent or the surface crosslinking agent solution without mixing with the surface crosslinking agent or the surface crosslinking agent solution; and (c) adding the additive at a stage previous to the surface crosslinking agent addition step, and is also a combination of at least two of these processes.

In a case where the surface crosslinking agent addition step and the additive addition step are each carried out twice or more times, it is more preferable that a last surface crosslinking agent addition step is followed by a last additive addition step, and it is still more preferable that a first surface crosslinking agent addition step is followed by a first additive addition step. It should be noted that in a case where the additive is added only once, the additive addition step is the first addition step and is also the last addition step.

This is exemplified by, for example, the following modes: a mode of carrying out the additive addition step after the surface crosslinking agent addition step; and a mode of simultaneously carrying out the surface crosslinking agent addition step and the additive addition step; a mode of simultaneously carrying out the surface crosslinking agent addition step and the additive addition step; a mode of simultaneously carrying out the surface crosslinking agent addition step and the additive addition step and then carrying out another additive addition step; and the like.

The additive addition step needs only to be carried out after the first surface crosslinking agent addition step. It is preferable that the additive addition step is carried out at least once after the surface crosslinking agent addition step is carried out at least once, and it is more preferable that the additive addition step is carried out once after all of the surface crosslinking agent addition steps.

The additive used in the present invention is an additive selected from water-insoluble fine particulate compounds and cationic compounds. The additive is used to exert effects of preferably a liquid permeability enhancer and an Anti-Caking agent, particularly preferably a liquid permeability enhancer. In consideration of a representative function of the additives, the additives described above and additives described below in the present invention may also be collectively referred hereinafter to as "liquid permeability enhancers."

(Liquid Permeability Enhancer)

The liquid permeability enhancer in the present invention is an additive selected from insoluble fine particulate compounds and polyvalent cationic compounds or an additive for increasing SFC or free swelling GBP (preferably obtaining SFC increase to fall within a range described below) as compared with SFC or free swelling GBP obtained when no liquid permeability enhancer is used. It should be noted that the term "GBP" is defined in WO 2004/096304.

The water-insoluble fine particulate compounds and cationic compounds in the present invention serve as a stereoscopic spacer or an electrostatic spacer on the surface of a water absorbent resin. The water-insoluble microparticulate compounds and cationic compounds in the present invention cause a resultant water absorbing agent to have "increased liquid permeability (for example, SFC (described later) increased by not less than $1 \times 10^{-7}$ ($cm^3 \cdot sec/g$), and further not less than $10 \times 10^{-7}$ ($cm^3 \cdot sec/g$) as compared with SFC obtained when these compounds are not used)," "increased Anti-Caking property (for example, blocking tendency at moisture absorption (described later) increased by not less than 1% or by not less than 5%)," "increased gel strength," "increased free swelling capacity (FSC) (for example, FSC (defined by ERT440.2-02) increased by 0.5 g/g or by not less than 1 g/g)." Besides, these additives, depending on their kinds, can achieve effects such as "deodorization/antibacterial activity" and "reduction of a residual surface crosslinking agent," but their effects and intended uses are not particularly limited in the present invention.

The additive or liquid permeability enhancer essentially added in the production method according to the present invention is preferably selected from water-insoluble inorganic fine particles and polyvalent cationic compounds (cationic polymer compounds or water-soluble polyvalent metal cation-containing compounds). The "water-soluble"

compound as used herein refers to a compound that dissolves, in 100 g of water (25° C.), in an amount of not less than 1 g or not less than 5 g. The "water-insoluble" compound refers to a compound that dissolves, in 100 g of water (25° C.), in an amount of less than 1 g, less than 0.5 g or less than 0.1 g.

In the present invention, while the organic surface cross-linking agent cross-links, by covalent bond, with a functional group of a water absorbent resin, the polyvalent cationic compound (cationic polymer compound or water-soluble polyvalent metal cation-containing compound) of the present invention is assumed to cross-link with a water absorbent resin by ion crosslinking or is assumed to serve as a stereoscopic spacer or as an electrostatic spacer, thereby increasing liquid permeability.

(Inorganic Fine Particles)

Examples of the inorganic fine particles include: water-insoluble fine particulate inorganic powder such as silicon dioxide, titanium dioxide, aluminium oxide, magnesium oxide, zinc oxide, talc, metal phosphate (e.g. calcium phosphate, barium phosphate, and aluminum phosphate), metal borate (e.g. titanium borate, aluminum borate, iron borate, magnesium borate, manganese borate, and calcium borate), silicic acid or salt thereof, clayey materials, diatomaceous earth, zeolite, bentonite, kaolin, hydrotalcite, and activated clay; and organic fine powders such as calcium lactate, aluminum lactate, a metal soap (polyvalent metal salt of long chain fatty acid). As for the inorganic fine particles, volume average particle diameter thereof is preferably not more than 10 μm, and more preferably not more than 1 μm.

The inorganic fine particles before mixed with a water absorbent resin may be in a form of powder or in a form of a water dispersion (slurry (e.g. colloidal silica)). Alternatively, the inorganic fine particles before mixed with a water absorbent resin may be in a form of being dispersed in a surface crosslinking agent or an aqueous solution of the surface crosslinking agent.

(Cationic Polymer Compound)

The cationic polymer compound is not particularly limited. However, the cationic polymer compound is suitably any of cationic polymer compounds described in U.S. Pat. Nos. 5,382,610, 7,098,284, WO2009/110645, WO2009/041731, WO2009/041727. Among the compounds described in the above-listed documents, polyethylene imine, polyvinyl amine, polyallylamine, or a condensate of dimethylamine, ammonia, and epichlorohydrin are preferable as the cationic polymer compound in the present invention.

As for a molecular weight of the cationic polymer compound, a weight average molecular weight is preferably in a range of 1,000 to 5,000,000, more preferably in a range of 2,000 to 1,000,000, and still more preferably in a range of 10,000 to 500,000.

The cationic polymer compound is preferably a water-soluble compound from the viewpoint of facilitating mixture. Here, the term "water-soluble" means that a compound dissolves in an amount of not less than 1 g in 100 g of water (25° C.).

The cationic polymer compound may be directly mixed with a water absorbent resin or may be mixed in a form of a solution, particularly in a form of an aqueous solution. Alternatively, the cationic polymer compound may be mixed in a form of being dissolved in a surface crosslinking agent or in an aqueous solution of the surface crosslinking agent.

(Water-soluble Polyvalent Metal Cation-containing Compound)

The water-soluble polyvalent metal cation-containing compound refers to a compound containing a bivalent or higher metal cation, preferably a trivalent or higher metal cation. The trivalent or higher metal cation is exemplified by aluminum, zirconium, and titanium. Among these, aluminum is preferable. Examples of the polyvalent metal cation-containing compound encompass (i) polyvalent metal compounds, which are inorganic surface crosslinking agents, including inorganic salts of polyvalent metals such as aluminum sulfate, aluminum chloride, zirconium chloride oxide, zirconium ammonium carbonate, zirconium potassium carbonate, zirconium sulfate, zirconium acetate, and zirconium nitrate, etc.; (ii) polyvalent metal compounds including organic salts of polyvalent metals such as aluminum acetate, aluminum lactate, hydroxy zirconium chloride, titanium triethanol aminate, and titanium lactate, etc.; and the like. Among these, a compound containing aluminum as the polyvalent metal cation is preferable.

These compounds may be directly mixed in a form of a powder with a water absorbent resin. Alternatively, they may be mixed in a form of a solution or a dispersion, particularly in a form of an aqueous solution. Further alternatively, they may be mixed in a form of being dissolved in a surface crosslinking agent or an aqueous solution of the surface crosslinking agent.

The amount of the additive or liquid permeability enhancer selected from the water-insoluble fine particulate compounds and polyvalent cationic compounds is preferably in a range of 0.001 parts by mass to 5 parts by mass, more preferably in a range of 0.01 parts by mass to 2 parts by mass, and still more preferably in a range of 0.01 parts by mass to 1 part by mass, relative to 100 parts by mass of a water absorbent resin to which the additive or liquid permeability enhancer is to be added. It should be noted that in a case where the additive or liquid permeability enhancer is the water-soluble polyvalent metal cation-containing compound, these values are expressed in terms of the amount of polyvalent metal cation (e.g. in a case of the aluminum sulfate, it is a value based on the amount of $Al^{3+}$).

In a production method according to the present invention, a water-soluble polyvalent metal cation-containing compound may be added twice or more times. For example, in a case where the water-soluble polyvalent metal cation-containing compound is added twice, a ratio between a first addition and a second addition is in a range of 1:99 to 99:1 and preferably in a range of 10:90 to 90:10. A ratio falling outside the above ranges is not preferable because it causes a situation extremely close to one-time addition, which reduces effectiveness of plurality of additions.

It should be noted that a non-metallic ion crosslinking agent such as a cationic polymer compound can express tackiness at the aforementioned mixture. In view of this, the addition of the non-metallic ion crosslinking agent is preferably performed after the last heat treatment.

In a case where a solvent is used for mixture of the water-soluble polyvalent metal cation-containing compound, the solvent is preferably water or an aqueous crosslinking agent solution. For the improvement in dispersity, solubility, and blendability, water may be used in combination with a hydrophilic organic solvent (alcohol or polyglycol) or a surfactant, if necessary. The amount of water used is appropriately determined according to a kind of additive and an addition method and is, for example, in a range of 0 part by mass (dry blending) to 50 parts by mass, in a range of 0.1 parts by mass to 10 parts by mass, or in a range of 0.5 parts by mass to 5 parts by mass, relative to 100 parts by mass of a water absorbent resin.

Further, as a liquid permeability enhancer other than the above liquid permeability enhancers, a water-soluble polysiloxane described in the pamphlet of International Publication No. WO 2009/093708, primary to tertiary amine compounds described in the pamphlet of International Publication No. WO 2008/108343, etc. can be preferably used.

(Step of Adding Other Additive(s))

The present step is a step of adding other additive(s) in order to impart various functions to a surface-crosslinked water absorbent resin and is composed of one step or a plurality of steps. As the additive, the aforementioned liquid permeability enhancer, a deodorant, a perfume, an antimicrobial agent, a foaming agent, a chelating agent, a surfactant, an anti-coloring agent, a pigment, a dye, a fertilizer, an oxidizing agent, a reducing agent, etc. may be contained for imparting or improving the functions. Water can be added as an additive for granulation. Water can be added as a solvent of the additive. Furthermore, drying can be carried out before addition of the additive.

These additives are used in such a manner that the proportion of these additives to surface-crosslinked water absorbent resin particles is less than 10 mass %, preferably less than 5 mass %, and more preferably less than 1 mass %. Further, the addition of these additives may be performed simultaneously with or separately from the surface crosslinking step.

[3] Physical Properties of Polyacrylic Acid (Salt)-based Water Absorbent Resin Powder (3-1) AAP (Absorption Capacity Under Load)

Surface crosslinking after the polymerization can be attained by, for example, a water absorbent resin powder that shows an absorption capacity (AAP) of not less than 15 (g/g), preferably not less than 17 (g/g), and more preferably not less than 19 (g/g) for a 0.9 mass % of sodium chloride aqueous solution under a load of 4.8 kPa. Higher AAP of the water absorbent resin powder is thus more preferable. However, from the viewpoint of a balance between the AAP and other properties (e.g. SFC), an upper limit of the AAP of the water absorbent resin powder is preferably not more than 40 (g/g), more preferably not more than 35 (g/g), and still more preferably not more than 30 (g/g). Note that AAP of a water absorbent resin powder can be controlled by surface crosslinking, CRC, and a liquid permeability enhancer.

(3-2) 0.58 psi PUP (Absorption Capacity Under Load)

Surface crosslinking after the polymerization can be attained by, for example, a water absorbent resin that shows an absorption capacity (PUP) of not less than 30 (g/g), preferably not less than 31 (g/g), and more preferably not less than 32 (g/g) for an aqueous solution of artificial urine under a load of 4.12 kPa. Higher PUP of the water absorbent resin is thus more preferable. However, from the viewpoint of a balance between the PUP and other properties (e.g. SFC), the water absorbent resin of the present invention is a water absorbent resin having PUP whose upper limit is preferably not more than 50 (g/g), more preferably not more than 45 (g/g), and still more preferably not more than 40 (g/g). Note that PUP can be controlled by surface crosslinking, CRC, and a liquid permeability enhancer.

(3-3) CRC (Absorption Capacity without Load)

A water absorbent resin in the present invention is a water absorbent resin having an absorption capacity without load (CRC) of not less than 20 (g/g), preferably not less than 23 (g/g), more preferably not less than 25 (g/g), and particularly preferably not less than 28 (g/g). In a case where the absorption capacity without load is low, water absorbing efficiency declines when the water absorbent resin is used in sanitary materials such as diapers becomes. Higher absorption capacity without load (CRC) is thus more preferable. However, from the viewpoint of a balance between the CRC and other properties (e.g. SFC), an upper limit of the absorption capacity without load is preferably not more than 60 (g/g), more preferably not more than 50 (g/g), and still more preferably not more than 35 (g/g). The CRC can be controlled by crosslinking density in a polymerization step and/or a surface crosslinking step.

(3-4) SFC (Saline Flow Conductivity)

The saline flow conductivity (SFC) depends on a water absorbent resin composition content (wt %) of a sanitary material. The higher the water absorbent resin composition content is, the higher saline flow conductivity (SFC) is required. From a viewpoint of a balance between the SFC and other properties (e.g. CRC), an upper limit of the SFC is approximately not more than $1000(\times 10^{-7} \text{ cm}^3 \cdot \text{sec/g})$. The SFC can be controlled by (i) the aforementioned particle size, (ii) CRC, and (iii) crosslinking density during polymerization or during surface crosslinking (particularly surface crosslinking density).

The polymerization and surface-crosslinking of particle-size adjusted particles can be attained by a water absorbent resin that shows 0.69 mass % saline flow conductivity (SFC) (which is permeability potential of a liquid under pressure) of not less than $10(\times 10^{-7} \text{ cm}^3 \cdot \text{sec/g})$, preferably not less than $15(\times 10^{-7} \text{ cm}^3 \cdot \text{sec/g})$, more preferably not less than $20(\times 10^{-7} \text{ cm}^3 \cdot \text{sec/g})$, still more preferably not less than $30(\times 10^{-7} \text{ cm}^3 \cdot \text{sec/g})$, further still more preferably not less than $50(\times 10^{-7} \text{ cm}^3 \cdot \text{sec/g})$, and particularly preferably not less than $70(\times 10^{-7} \text{ cm}^3 \cdot \text{sec/g})$.

(3-5) Extr.

Extr. (water soluble component) of the water absorbent resin and the water absorbing agent obtained by the present invention is preferably in a range of 5 mass % to 20 mass %, more preferably in a range of 5 mass % to 18 mass %, and still more preferably in a range of 5 mass % to 15 mass %. In a case where the Extr. exceeds 20 mass %, a get strength of an obtained water absorbent resin or an obtained water absorbing agent is weak. This may cause inferior liquid permeability. In a case where such a water absorbent resin is used for a water absorbent body such as a diaper, it may not be possible to obtain a water absorbent resin having little amount of rewetting when pressure is applied to the water absorbent body.

Extr. can be controlled as necessary by the aforementioned internal crosslinking agent or the like. Note, however, that a water absorbent resin or a water absorbing agent having an Extr. of less than 5 mass % is not preferable because such a water absorbent resin or water absorbing agent (i) requires a large amount of internal crosslinking agent to be produced, (ii) causes an increase in cost and the occurrence of remaining crosslinking agent beyond the limit of detection, and (iii) causes significant deterioration of the CRC.

(3-6) Surface Soluble Component

Surface soluble component of the water absorbent resin and the water absorbing agent to be obtained by the present invention is preferably in a range of 0 mass % to 4.5 mass %, more preferably in a range of 0 mass % to 3.5 mass %, and particularly preferably in a range of 0 mass % to 3.0 mass %. If the surface soluble component exceeds 4.5 mass %, then a large amount of surface-crosslinked layer breaks due to swelling, thereby causing the surface-crosslinked layer to be weak. This poses a risk of causing a decrease in absorption capacity under load by addition of a liquid permeability enhancer to be large. Note that the surface soluble component can be appropriately controlled by the aforementioned internal crosslinking agent, the surface crosslinking, and the dew point during the surface treatment.

(3-7) Surface-crosslinked Layer Strength Index

A surface-crosslinked layer strength index of the water absorbent resin and the water absorbing agent to be obtained by the present invention is preferably not more than 40, more preferably not more than 35, even more preferably not more than 30, and particularly preferably not more than 25. If the surface-crosslinked layer strength index exceeds 40, then an amount of decrease in AAP as a result of addition of a liquid permeability enhancer becomes large. This poses a risk of causing defects such as a large amount of leakage when the water absorbing agent is used for a sanitary material such as a disposable diaper. A lower surface-crosslinked layer strength index is more preferable, and a lower limit is 0. However, from the viewpoints of a balance between (i) the surface-crosslinked layer strength index and (ii) other properties and production cost, the lower limit may be approximately 5, or, depending on a case, may be approximately 10.

(3-8) Particle Size Distribution and Additive for Functionalization

There are no limitations on particle diameter and particle size distribution of the water absorbent resin and the water absorbing agent obtained by the present invention. However, it is preferable to obtain, by particle sizing after addition and mixing of a final surface crosslinking agent, a water absorbent resin and a water absorbing agent having particle diameter of less than 1 mm or even the following particle diameter. Assume that a large amount of particles having a diameter of not less than 1 mm, especially not less than 850 μm, is contained in a water absorbent resin and a water absorbing agent. In this case, if such large-size particles are used for especially a thin sanitary material/absorbent article, not only the large-size particles cause uncomfortableness of a user wearing the thin sanitary material/absorbent article, but also a water impermeable material (known as a back sheet) constituting an absorbing product becomes damaged by abrasion and therefore may cause leakage of urine or the like in actual use. Hence, such large-size particles are not preferable. Therefore, particles having not less than 850 μm are preferably little in amount. The particles having diameters of not less than 850 μm are preferably in a range of 0 mass % to 5 mass %, more preferably in a range of 0 mass % to 3 mass %, still more preferably in a range of 0 mass % to 1 mass %, and particularly preferably not contained at all in practice. Furthermore, the amount of contained large-size particles having diameters of not less than 710 μm are preferably in a range of 0 mass % to 20 mass %, more preferably in a range of 0 mass % to 10 mass %, still more preferably in a range of 0 mass % to 5 mass %, further still more preferably in a range of 0 mass % to 3 mass %, and particularly preferably in a range of 0 mass % to 1 mass %.

On the other hand, a percentage of fine particles having diameters of less than 150 μm is preferably in a range of 0 mass % to 3.0 mass %, more preferably in a range of 0 mass % to 2.0 mass %, and still more preferably in a range of 0 mass % to 1.5 mass %.

Furthermore, while maintaining the above ranges, particles having diameters of not less than 150 μm and less than 850 μm, more preferably not less than 150 μm and less than 710 μm, are preferably contained to be not less than 95 mass % (upper limit: 100 mass %), more preferably not less than 98 mass %, still more preferably not less than 99 mass %, and most preferably contained in their entirety in practice.

A weight average particle diameter (defined by standard sieve classification) of water absorbent resin particles of a water absorbing agent to be obtained as a final product after the above steps in the present invention is preferably not less than 200 μm and not more than 600 μm, more preferably in the range of 200 μm to 550 μm in order to improve its performance, still more preferably in the range of 250 μm to 500 μm, and most preferably in the range of 350 μm to 450 μm. A percentage of particles having particle diameters of less than 300 μm is preferably not less than 10 mass %, more preferably in the range of 10 mass % to 50 mass %, and still more preferably in the range of 10 mass % to 30 mass %.

A moisture content of a water absorbing agent (weight decrease rate at 180° C. in three hours) is preferably in a range of 0 mass % to 15 mass %, more preferably in a range of 0.1 mass % to 10 mass %, still more preferably in a range of 0.5 mass % to 8 mass %.

Particle size can be controlled as necessary by pulverizing, classification (pre-surface crosslinking and post-surface crosslinking), granulation, and the like.

[4] Use or the Like of Particulate Water Absorbing Agent

In a case where the above ranges are not maintained, it may not be possible to obtain a balanced water absorbent resin having excellent liquid permeability while maintaining desired absorption capacity. Particularly, particles having particle diameters of less than 150 μm are preferably as little as possible in amount because such particles not only cause a reduction in liquid permeability, but also may cause adverse effect by generating dust etc. in an environment where an absorbent article as a material for a water absorbent resin is produced.

The water absorbing agent of the present invention preferably contains, other than surface-crosslinked water absorbent resin particles, (i) a liquid permeability enhancer or (ii) an additive selected from water-insoluble fine particulate compounds and polyvalent cationic compounds. Furthermore, the water absorbing agent of the present invention can have imparted or increased functionality by containing additives such as a deodorant, a perfume, an antimicrobial agent, a foaming agent, a chelating agent, a surfactant, an anti-coloring agent, a pigment, a dye, a fertilizer, an oxidizing agent, and a reducing agent. A percentage of such additives used relative to a total amount of water absorbent resin particles and water-soluble polyvalent metal salt particles is less than 10 mass %, preferably less than 5 mass %, and more preferably less than 1 mass %.

The water absorbent resin of the present invention is to be used for sanitary materials such as disposable diapers sanitary napkins, incontinence pads, and medical pads. In a case where the water absorbent resin of the present invention is used for a sanitary material, the sanitary material to be used preferably includes (a) a liquid permeable top sheet positioned next to a body of a user, (b) a liquid-impermeable back sheet positioned away from the body of the user and positioned next to clothing of the user, and (c) a water absorbent body positioned between the top sheet and the back sheet. The water absorbent body can be made up of two or more layers, or can be used in combination with a pulp layer etc.

In the case where the water absorbent resin of the present invention is used for a sanitary material, a gel having absorbed liquid is unlikely to cause so-called gel blocking, and therefore spaces between gels are not blocked as a result of the gels in close contact with each other. Hence, even in a case where the water absorbent resin is used at high concentration in an absorbent body such as a diaper, urine and bodily fluids discharged for second or subsequent times can be spread out inside the absorbent body without being stuck on a surface of the absorbent body. This allows the urine and the bodily fluids to be distributed throughout the water absorbent resin inside the absorbent body.

EXAMPLES

The following description will discuss the invention with reference to Examples, Comparative Examples, and Reference Examples. However, interpretation of the present invention should not be limited by the examples or the like. Physical properties described in the Claims and the examples of the present invention were calculated (i) by the methods described in the sections (5-1) through (5-7), (ii) at room temperature (23±2° C.), and (iii) at a humidity of 50±10 RH %. Note that unless specified otherwise, each step in each example was carried out under substantially atmospheric pressure (atmospheric pressure ±5%, more preferably ±1%), and was carried out without changing pressure by intentionally increasing or decreasing the pressure in the same step.

(5-1) Absorption Capacity without Load (CRC)

In accordance with ERT441.2-0.2, 0.200 g of water absorbent resin was allowed to freely swell in a large excess of a 0.90 wt % of sodium chloride aqueous solution (also referred to as "physiological saline") without load for 30 minutes. Then, an absorption capacity (CRC) after water was drained by centrifugal separation was measured.

(5-2) Absorption Capacity Under Load (AAP/Absorbency Against Pressure)

In accordance with the absorption capacity under load evaluation method disclosed in the publication of EDANA (European Disposables and Nonwovens Association) and the method described in ERT442.2-02, a one-hour measurement was carried out with use of 0.900 g of water absorbent resin and a 0.9 mass % of sodium chloride aqueous solution, and absorption capacity under load (g/g) of water absorbent resin was calculated under such excessive load as 4.83 kPa (approximately 0.7 psi).

(5-3) Liquid Permeability (SFC)

SFC was measured by the method which is disclosed in the pamphlet of International Publication No. WO 95/26209, and is well known.

(5-4) Absorption Capacity Under Load (0.58 psi PUP)

A 400-mesh metal net made of stainless steel (mesh size: 38 μm) was fused to a bottom of a plastic supporting cylinder having an inner diameter of 60 mm. Then, under conditions of room temperature (25±2° C.) and a humidity of 50 RH %, 0.900 g of water absorbent resin was uniformly spread on the metal net. Then, a piston and a weight were placed in this order.

The piston had an external diameter of slightly shorter than 60 mm, so that (i) a gap between the piston and an inner wall of the supporting cylinder could not be made and (ii) vertical movements of the piston were free. The weight was adjusted so that it was possible to uniformly apply a load of 4.12 kPa (approximately 0.58 psi) to a water absorbent resin.

Then, a total weight Wa (g) of the entire measuring apparatus was measured.

Then, a glass filter (manufactured by Sogo-Rikagaku Glass Production Co., Ltd., micropore diameter: 100 μm to 120 μm) having a diameter of 90 mm and a thickness of 5 mm was placed in a petri dish having a diameter of 150 mm. Then, artificial urine (1) (20° C. to 25° C.) was added to be at an equal level to a top surface of the glass filter.

Then, the entire measuring apparatus was placed on the glass filter, the artificial urine (1) (composition: aqueous solution of 0.2 mass % sodium sulfate, 0.2 mass % potassium chloride, 0.05 mass % magnesium chloride hexahydrate, 0.025 mass % calcium chloride dihydrate, 0.085 mass % ammonium di-hydrogen phosphate, and 0.015 mass % di-ammonium hydrogen phosphate) was allowed to absorb water for a predetermined period of time under load.

Note that in a case where a liquid level of the artificial urine (1) fell lower than the top surface of the glass filter, the artificial urine (1) was further added to maintain a constant liquid level. After one hour passed since the start of the measurement, the entire measuring apparatus was taken out, and a weight Wb (g) of the entire measuring apparatus thus taken out was measured. Note that it is necessary to measure the weight as quickly as possible without causing any vibration. Next, absorption capacity under load (g/g) was calculated based on the weights Wa and Wb thus measured.

The measurement method was in accordance with the PUP measurement method disclosed in the pamphlet of International Publication No. WO 95/26209, except that an applied load was changed.

(5-5) 16-hour Soluble Component (Extr.)

Measurement was carried out in accordance with the water soluble component evaluation method disclosed in the publication of EDANA (European Disposables and Nonwovens Association) and the method described in ERT470.2-02.

Specifically, 200 g of 0.90 mass % saline was measured and put in a plastic container of 250 ml in capacity with a lid, thereby obtaining an aqueous solution. Then, 1.00 g of water absorbent resin particles or water absorbing agent was added to the aqueous solution, thereby obtaining a mixture. Then, the mixture was stirred at 500±50 rpm by use of a stirrer (length: 3.5 cm) for 16 hours, thereby extracting soluble component in the water absorbent resin or water absorbing agent (mainly soluble polyacrylate and the like).

This extract was filtered by use of a sheet of filter paper (manufactured by ADVANTEC TOYO KAISHA LTD., Product name: (JIS P 3801, No. 2), thickness: 0.26 mm, retaining particle diameter: 5 μm), thereby obtaining a filtrate. 50.0 g of the filtrate was measured so that a measurement solution was prepared.

First, 0.90 mass % saline was titrated with the use of 0.1 N NaOH aqueous solution until it reached pH10. Then, the saline was titrated with the use of 0.1 N HCl aqueous solution until it reached pH2.7, thereby obtaining control titres ([bNaOH] ml, [bHCl] ml).

The measurement solution was also titrated in the same manner, thereby obtaining titres [NaOH] ml, [HCl] ml).

In a case of, for example, water absorbent resin particles or water absorbing agent which include(s) a known amount of acrylic acid and sodium salt, soluble component of the water absorbent resin particles or of the water absorbing agent can be calculated (i) based on an average molecular weight of monomers and on titres obtained by the aforementioned titration and (ii) by the following equation:

soluble component (mass %)=0.1×(average molecular weight)×200×100×([HCl]−[bHCl])/1000/1.0/50.0

In a case where the amount of acrylic acid and sodium salt is unknown, an average molecular weight of monomers is calculated with a neutralization rate obtained by titration.

(5-6) Surface Soluble Component 25 g of 0.90 mass % saline was measured and put in a plastic container of 250 ml in capacity with a lid, thereby obtaining an aqueous solution. To the aqueous solution, 1.00 g of water absorbent resin particles or of water absorbing agent was/were uniformly added. The container was closed with the lid and was allowed to stand for 1 hour. Then, 75 g of 0.90 mass % saline was added, and a resultant solution was stirred for 1 minute with a stirrer and at a rotation speed which were identical to those of (5-5). Then, soluble component seeping from a resultant water absorbent resin or water absorbing agent was extracted. The extract was filtered with a sheet of filter paper (manufactured by ADVANTEC TOYO KAISHA LTD., Product name: (JIS P 3801, No. 2), thickness: 0.26 mm, retaining particle diameter: 5 μm). 50.0 g of the filtrate was measured, so that a measurement solution was prepared.

First, only 0.90 mass % saline was titrated with 0.1 N NaOH aqueous solution until it reached pH10. Then, the saline was titrated with 0.1 N HCl aqueous solution until it reached pH 2.7, thereby obtaining titres ([bNaOH] ml, [bHCl] ml).

The measurement solution was also titrated in the same manner, thereby obtaining titres [NaOH] ml, [HCl] ml).

In a case of, for example, water absorbent resin particles or water absorbing agent which include(s) a known amount of acrylic acid and sodium salt, surface soluble content of the water absorbent resin particles or of the water absorbing agent can be calculated (i) based on an average molecular weight of monomers and on titres obtained by the aforementioned titration and (ii) by the following equation:

Surface soluble component (mass %)=0.1×(average molecular weight)×100×100×([HCl]−[bHCl])/ 1000/1.0/50.0

In a case where the amount of acrylic acid and sodium salt was unknown, an average molecular weight of monomers was calculated with a neutralization rate obtained by titration.

(5-7) Surface-crosslinked Layer Strength Index

A ratio of surface soluble component to the soluble component thus measured earlier was calculated by the following equation:

surface-crosslinked layer strength index=surface soluble component(%)/Extr(%)×100

Reference Example 1

A solution (A) was prepared by mixing 421.7 g of acrylic acid, 1.83 g of polyethyleneglycol diacrylate (weight average molecular weight: 523, the polyethyleneglycol diacrylate as an internal crosslinking agent is such that the average number (n) of moles of ethylene oxide added is 9) (0.06 mol %), and 1.29 g of a 2 mass % of diethylentriamine pentaacetate trisodium aqueous solution (manufactured by CHELEST CORPORATION). A NaOH aqueous solution (B) was prepared by diluting 352.3 g of a 48.5 mass % NaOH of aqueous solution with 402.7 g of ion exchange water.

While the solution (A) was stirred with a magnetic stirrer, the aqueous solution (B) was added to the solution (A) all at once in an open system, and was mixed. Although an educt was observed at the beginning of the mixing, the educt was immediately dissolved, thereby obtaining a monomer aqueous solution (monomer concentration: 43 mass %, neutralization rate: 73 mol %). Then, to the monomer aqueous solution, 19.4 g of a 3.6 mass % of sodium persulfate aqueous solution was added. A resultant solution was stirred for several seconds, and immediately placed on a hot plate set to a temperature of 90° C. Then, in an open system, the solution was poured into a stainless vat having an inner surface to which a silicon sheet was attached. The stainless vat has a bottom surface measuring 200 mm×260 mm, a top surface measuring 560 mm×460 mm, and a height of 140 mm. A vertical cross section of the stainless vat has a trapezoidal shape when passing through a center part of the stainless vat. Polymerization was initiated while the top surface of the stainless vat was opened.

The polymerization proceeded while the solution was generating water vapors, foaming, and expanding, so that a hydrous polymer was generated. After the polymerization, the hydrous polymer was taken out from the stainless vat. The hydrous polymer was divided equally into 16 pieces. Then, the pieces of the hydrous polymer were crushed by introducing the pieces, one piece for every 10 seconds, into a meat chopper (manufactured by REMACOM HL-3225N) having a dice of 9.5 mmΦ while 50 g of ion exchange water was added each minute.

The hydrous polymer, which had been crushed and grain-refined, was spread on a 50-mesh metal net (having mesh size of 300 μm), and was dried by hot-air drying at a temperature of 190° C. for 50 minutes. In this manner, a particulate or powdery irregular-shaped water absorbent resin that can be easily pulverized or a water absorbent resin in the form of particulate dry aggregates was obtained. The water absorbent resin thus obtained was pulverized with a roll mill, and classified with the use of a JIS standard sieve having mesh size of 850 μm. Particles remaining on the sieve were removed.

Next, as in the aforementioned operations, particles passing through the JIS standard sieve having mesh size of 850 μm were classified with the use of a JIS standard sieve having mesh size of 150 μm, thereby obtaining a water absorbent resin passing through the JIS standard sieve having mesh size of 150 μm. In this manner, a particulate water absorbent resin (1) was obtained. CRC and soluble component of the water absorbent resin (1) thus obtained were 35.2 g/g and 12.0%, respectively.

Example 1

Relative to 100 parts by mass of the water absorbent resin (1) obtained in Reference Example 1, 4.1 parts by mass of surface treatment agent mixture solution containing 2-oxo-1,3-dioxolane, 1,2-propanediol, and ion exchange water (in a mixture ratio (mass ratio) of 0.4:0.7:3.0) was added and mixed.

In the mixing, a Loedige mixer (manufactured by Gerbrueder Ledige Maschibenbau GmbH) was used as a mixer. The water absorbent resin (1) and a surface treatment agent mixture solution were mixed together by spraying the surface treatment agent mixture solution onto the water absorbent resin (1) with the use of a spray nozzle (single-fluid hollow cone nozzle (1/4M-K-008) manufactured by H. IKEUCHI Co., Ltd.).

A resultant mixture was evenly spread on a SUS vat. The SUS vat was allowed to stand in a drying apparatus in which an atmospheric temperature and a dew point were conditioned to be at 197° C. and 90° C., respectively, as measured by Humidity and Temperature Transmitter HMT337 (manufactured by VAISALA). Then, a heat treatment was carried out for 30 minutes.

Particles after the heat treatment were allowed to pass through a JIS standard sieve having mesh size of 850 μm, thereby obtaining a surface-crosslinked water absorbent resin (1), the periphery of a surface of which has been crosslinked properties of the surface-crosslinked water absorbent resin (1) thus obtained are shown in Table 2.

Relative to 100 parts by mass of the surface-crosslinked water absorbent resin (1) thus obtained, 1.2 parts by mass of aluminum sulfate mixture solution was added, which aluminum sulfate mixture solution contains a 27 mass % of aluminum sulfate aqueous solution (8 mass % based on aluminum oxide), a 60 mass % of sodium lactate aqueous solution, and 1,2-propylene glycol (in a mixture ratio (mass ratio) of 1:0.3:0.025). After the addition, a resultant mixture was dried at 60° C. for 1 hour with no air flow.

Next, resultant particles were allowed to pass through a JIS standard sieve having mesh size of 850 μm, thereby obtaining a water absorbing agent (2). Physical properties of the surface-crosslinked water absorbing agent (1) and of the water absorbing agent (2) thus obtained are shown in Table 2.

Example 2

The same operations as in Example 1 were carried out except that the atmospheric dew point during a heat treatment was changed to 70° C., so that a surface-crosslinked water absorbent resin (3) and a water absorbing agent (4) were obtained. The physical properties of the surface-crosslinked water absorbent resin (3) and the water absorbing agent (4) thus obtained are shown in Table 2.

Comparative Example 1

The same operations as in Example 1 were carried out except that (i) the atmospheric dew point during a heat treatment was changed to 40° C. and (ii) the heating time for a surface crosslinking treatment was changed to 20 minutes. In this manner, a surface-crosslinked water absorbent resin (5) and a water absorbing agent (6) were obtained. The physical properties of the surface-crosslinked water absorbent resin (5) and the water absorbing agent (6) thus obtained are shown in Table 2.

Example 3

The same operations as in Example 1 were carried out except that (i) the surface treatment agent mixture solution was changed to 2.4 parts by mass of 2-oxazolidone, 1,2-propanediol, ion exchange water, and isopropyl alcohol (mixture ratio (mass ratio) of 0.1:0.1:1.6:0.6), (ii) the atmospheric dew point during a heat treatment was changed to 70° C., and (iii) the heating time for a surface crosslinking treatment was changed to 20 minutes. In this manner, a surface-crosslinked water absorbent resin (7) and a water absorbing agent (8) were obtained. The physical properties of the surface-crosslinked water absorbent resin (7) and the water absorbing agent (8) thus obtained are shown in Table 2.

Comparative Example 2

The same operations as in Example 3 were carried out except that the dew point during a heat treatment was changed to 20° C., so that a surface-crosslinked water absorbent resin (9) and a water absorbing agent (10) were obtained. The physical properties of the surface-crosslinked water absorbent resin (9) and the water absorbing agent (10) thus obtained are shown in Table 2.

Example 4

The same operations as in Example 2 were carried out except that the heating time during the heat treatment during the step of obtaining the surface-crosslinked water absorbent resin (3) was changed to 20 minutes, so that a surface-crosslinked water absorbent resin (11) was obtained.

1.2 parts by mass of ion exchange water was added to 100 parts by mass of the surface-crosslinked water absorbent resin (11) thus obtained. Then, a resultant product was dried at 60° C. in a sealed state with no air flow for 1 hour. The resultant particles were allowed to pass through a JIS standard sieve having mesh size of 850 μm. To the resultant particles, 0.1 parts by mass of Aerosil 200CF-5 (Manufactured by Nippon Aerosil Co., Ltd.) was added, thereby obtaining a water absorbing agent (12). The physical properties of the surface-crosslinked water absorbent resin (11) and the water absorbing agent (12) thus obtained are shown in Table 2.

Comparative Example 3

The same operations as in Example 2 were carried out except that, during the step of obtaining the surface-crosslinked water absorbent resin (3), (i) the heating time during the heat treatment was changed to 20 minutes and (ii) the dew point was changed to 20° C. In this manner, a surface-crosslinked water absorbent resin (13) was obtained. 1.2 parts by mass of ion exchange water was added to 100 parts by mass of the surface-crosslinked water absorbent resin (13) thus obtained. Then, a resultant product was dried for 60° C. in a sealed state with no air flow for 1 hour. Particles obtained were allowed to pass through a JIS standard sieve having mesh size of 850 μm. To the resultant particles, 0.1 parts by mass of Aerosil 200CF-5 (Manufactured by Nippon Aerosil Co., Ltd.) was added, thereby obtaining a water absorbing agent (14). The physical properties of the surface-crosslinked water absorbent resin (13) and the water absorbing agent (14) thus obtained are shown in Table 2.

Example 5

Relative to 100 parts by mass of the surface-crosslinked water absorbent resin (11) obtained in Example 4, 0.45 parts by mass of a mixture solution in which (i) a dimethylamine-ammonia-epichlorohydrin resin aqueous solution (manufactured by SENKA Corporation, UNISENCE KHE102L that is an aqueous solution having average molecular weight of approximately 70,000, 1% aqueous solution pH of approximately 6, and solid content concentration of 50 mass %) and (ii) methanol were mixed with each other (in a mixture ratio (mass ratio) of 1:1) was added. The resultant product was dried at 90° C. for 1 hour. Particles obtained were allowed to pass through a JIS standard sieve having mesh size of 850 μm, thereby obtaining a water absorbing agent (15). The physical properties of the water absorbing agent (15) thus obtained are shown in Table 2.

Comparative Example 4

Relative to 100 parts by mass of the surface-crosslinked water absorbent resin (13) obtained in Comparative Example 3, 0.45 parts by mass of a mixture solution in which (i) a dimethylamine-ammonia-epichlorohydrin resin aqueous solution (manufactured by SENKA Corporation, UNISENCE KHE102L that is an aqueous solution having average molecular weight of approximately 70,000, 1% aqueous solution pH of approximately 6, and solid content concentration of 50 mass %) and (ii) methanol were mixed with each other (in a mixture ratio (mass ratio) of 1:1) was added. The resultant product was dried at 90° C. for 1 hour. Particles obtained were allowed to pass through a JIS standard sieve having mesh size of 850 µm, thereby obtaining a water absorbing agent (16). The physical properties of the water absorbing agent (16) thus obtained are shown in Table 2.

Reference Example 2

The same operations as in Reference Example 1 were carried out except that (i) the amount of polyethyleneglycol diacrylate was changed to 3.06 g (0.10 mol %) and (ii) the JIS standard sieve having mesh size of 850 µm used in the classification step after the pulverization with use of a roll mill was changed to a sieve having a mesh size of 710 µm. In this manner, a water absorbent resin (2) was obtained. As for the water absorbent resin (2), CRC was 33.0 g/g, and soluble component was 8.5%.

Example 6

The same operations as in Example 1 were carried out except that (i) the water absorbent resin (1) used in Example 1 was replaced by the water absorbent resin (2) obtained in Reference Example 2 and (ii) the heat treatment time was extended to 40 minutes. In this manner, a surface-crosslinked water absorbent resin (17) and a water absorbing agent (18) were obtained. The physical properties of the surface-crosslinked water absorbent resin (17) and the water absorbing agent (18) thus obtained are shown in Table 2.

Comparative Example 5

The same operations as in Example 6 were carried out except that (i) the dew point during the heat treatment was changed to 40° C. and (ii) the heat treatment time was changed to 30 minutes. In this manner, a surface-crosslinked water absorbent resin (19) and a water absorbing agent (20) were obtained. The physical properties of the surface-crosslinked water absorbent resin (19) and the water absorbing agent (20) thus obtained are shown in Table 2.

Comparative Example 6

In accordance with Example 1 of the pamphlet of International Publication No. WO 00/53664 except that 100 parts by mass of the water absorbent resin (2) obtained in Reference Example 2 of the present invention was used instead of 100 g of powder A disclosed in Example 1 of the pamphlet, 4.5 parts by mass of a surface treatment agent mixture solution containing a liquid permeability enhancer and containing 2-oxo-1,3-dioxolane, ion exchange water, and aluminum sulfate octadecahydrate (in a mixture ratio (mass ratio) of 1:3:0.5) was mixed with 100 parts by mass of the water absorbent resin (2) while being vigorously stirred. A resultant mixture was allowed to stand in a drying apparatus in which an atmospheric temperature and a dew point were conditioned to be at 180° C. and 35° C., respectively, as measured by Humidity and Temperature Transmitter HMT337 manufactured by VAISALA. Then, a heat treatment was carried out for 30 minutes, thereby obtaining a water absorbing agent (21). The physical properties of the water absorbing agent (21) thus obtained are shown in Table 2.

Example 7

The same operations as in Comparative Example 6 were carried out except that the dew point during the heat treatment in the step of obtaining the surface-crosslinked water absorbent resin (21) was changed to 70° C. In this manner, a surface-crosslinked water absorbent resin (22) was obtained. The physical properties of the surface-crosslinked water absorbent resin (22) thus obtained are shown in Table 2.

Reference Example 3

The same operations as in Reference Example 1 were carried out except that the amount of polyethyleneglycol diacrylate was changed to 0.90 g (0.03 mol %). In this manner, a water absorbent resin (3) was obtained. As for the water absorbent resin (3) thus obtained, CRC was 47.0 g/g, and soluble component was 16.1%.

Example 8

The same operations as in Example 1 were carried out except that the water absorbent resin (1) used in Example 1 was replaced by the water absorbent resin (3) obtained in Reference Example 3. In this manner, a surface-crosslinked water absorbent resin (23) and a water absorbing agent (24) were obtained. The physical properties of the surface-crosslinked water absorbent resin (23) and the water absorbing agent (24) thus obtained are shown in Table 2.

Comparative Example 7

The same operations as in Comparative Example 1 were carried out except that the water absorbent resin (1) used in Comparative Example 1 was replaced by the water absorbent resin (3) obtained in Reference Example 3. In this manner, a surface-crosslinked water absorbent resin (25) and a water absorbing agent (26) were obtained. The physical properties of the surface-crosslinked water absorbent resin (25) and the water absorbing agent (26) thus obtained are shown in Table 2.

Comparative Example 8

An experiment was conducted by reference to Example 1 of International Publication No. WO 2005/080479. According to Comparative Example 8 of the present invention, the water absorbent resin (2) obtained in Reference Example 2 instead of the base polymer taught in Example 1 of the international publication was sprayed with and mixed with two types of post-crosslinked solutions (post-crosslinked solution B and post-crosslinked solution C) with the use of the mixer and two of the spray nozzle described in Example 1.

The post-crosslinked solution B contains 2-oxazolidinone, isopropyl alcohol, 1,2-propanediol, and ion exchange water (in a ratio of 5.0:23.6:5.0:66.4). 2.42 parts by mass of the post-crosslinked solution B was sprayed onto 100 parts by mass of the water absorbent resin (2). Meanwhile, 1.08 parts by mass of a 23.0 mass % of aluminum sulfate aqueous solution, which is the post-crosslinked solution C, was sprayed onto 100 parts by mass of water absorbent resin (2) with the use of another spray nozzle and mixed.

A resultant mixture was uniformly dispersed on an SUS pallet, and the SUS pallet was introduced into a drying apparatus in which an atmospheric temperature and a dew point were conditioned to be at 180° C. and 20° C., respectively. Then, a heat treatment was carried out for 45 minutes, thereby obtaining a water absorbing agent (27). A temperature of the water absorbing agent (27) immediately after it was taken out from the drying apparatus was approximately 180° C. The physical properties of the water absorbing agent (27) thus obtained are shown in Table 2.

Example 9

The same operations as in Comparative Example 8 were carried out except that the dew point was changed to 80° C. In this manner, a water absorbing agent (28) was obtained. The physical properties of the water absorbing agent (28) thus obtained are shown in Table 2.

Example 10

The same operations as in Example 1 were carried out except that (i) the water absorbent resin (1) used in Example 1 was replaced by the water absorbent resin (2) obtained in Reference Example 2 and (ii) the dew point during the heat treatment and the heat treatment time were changed to 95° C. and 45 minutes, respectively, in the step of obtaining the surface-crosslinked water absorbent resin (3). In this manner, a surface-crosslinked water absorbent resin (29) was obtained.

Relative to 100 parts by mass of the surface-crosslinked water absorbent resin (29) thus obtained, 4 parts by mass of a mixture solution in which (i) a dimethylamine-ammonia-epichlorohydrin resin aqueous solution (manufactured by SENKA Corporation, UNISENCE KHE102L that is an aqueous solution having average molecular weight of approximately 70,000, 1% aqueous solution pH of approximately 6, and solid content concentration of 50 mass %) and (ii) methanol were mixed with each other (in a mixture ratio (mass ratio) of 1:1) was added. After the addition, a resultant product was dried at 90° C. with no air flow for 1 hour.

Then, a resultant product was allowed to pass through a JIS standard sieve having mesh size of 850 μm, so that a water absorbing agent (30) was obtained. The physical properties of the surface-crosslinked water absorbent resin (29) and the water absorbing agent (30) thus obtained are shown in Table 2.

Example 11

The same operations as in Example 10 were carried out except that the heat treatment time was changed to 55 minutes, so that a surface-crosslinked water absorbent resin (31) and a water absorbing agent (32) were obtained. The physical properties of the surface-crosslinked water absorbent resin (31) and the water absorbing agent (32) thus obtained are shown in Table 2.

Comparative Example 9

The same operations as in Example 10 were carried out except that (i) the dew point during the heat treatment was changed to 35° C. and (ii) the heat treatment time was changed to 30 minutes. In this manner, a surface-crosslinked water absorbent resin (33) and a water absorbing agent (34) were obtained. The physical properties of the surface-crosslinked water absorbent resin (33) and the water absorbing agent (34) thus obtained are shown in Table 2.

Reference Example 4

In a reactor formed by attaching a lid to a double-arm type stainless kneader having a capacity of 10 liters and equipped with two sigma type blades and a jacket, 11.9 g of (0.1 mol %) polyethyleneglycol diacrylate was dissolved in 5432.0 g of an aqueous solution of sodium acrylate (monomer concentration: 39 mass %) having neutralization rate of 73 mol %, so that a reaction solution was prepared. Next, the reaction solution was degassed in a nitrogen gas atmosphere for 30 minutes. Subsequently, 29.36 g of a 10 mass % of sodium persulfate aqueous solution and 24.5 g of a 0.1 mass % of L-ascorbic acid aqueous solution were added to the reaction solution with stirring. Approximately one minute after the addition, polymerization started. Then, a generated gel was polymerized at a temperature in the range of 20° C. to 95° C. while being crushed. 30 minutes after the polymerization was started, a generated water-containing gel-like crosslinked polymer was taken out. The water-containing gel-like crosslinked polymer thus obtained was grain-refined into fine pieces having a particle diameter of not more than approximately 5 mm. The water-containing gel-like crosslinked polymer, which was thus grain-refined into fine pieces, was spread on a 50-mesh metal net (having mesh size of 300 μm), and was subjected to hot-air drying at 180° C. for 50 minutes. A resultant water absorbent resin was pulverized with a roll mill, and was classified with JIS standard sieves having mesh size of 600 μm and 300 μm. Then, a particle size distribution was adjusted, so that a water absorbent resin (4) was obtained. As for the water absorbent resin (4) thus obtained, CRC was 35.2 g/g, soluble component was 8.5 wt %, and a mass average particle diameter was 450 μm.

Example 12

The same operations as in Example 1 were carried out except that (i) the water absorbent resin (1) was replaced by the water absorbent resin (4), (ii) the surface treatment agent mixture solution was changed such that ethyleneglycol diacrylate, 1,3-propanediol, and water (in a mixture ratio (mass ratio) of 0.04:1.0:2.6) was contained in an amount of 3.64 parts by mass, (iii) the atmospheric dew point during the heat treatment was changed to 80° C., (iv) the heating time for a surface crosslinking treatment was changed to 40 minutes, and (v) the sieve used in Example 1 after the addition of the mixture solution in which 27 mass % aluminum sulfate aqueous solution, 60 mass % sodium lactate aqueous solution, and 1,2-propylene glycol (in a mixture ratio (mass ratio) of 1:0.3:0.025) were contained was changed to a sieve having mesh size of 600 μm. In this manner, a surface-crosslinked water absorbent resin (35) and a water absorbing agent (36) were obtained. The physical properties of the surface-crosslinked water absorbent resin (35) and the water absorbing agent (36) thus obtained are shown in Table 4.

Comparative Example 10

The same operations as in Example 12 were carried out except that (i) the dew point was changed from 80° C. to 40° C. and (ii) the heat treatment time was changed from 40 minutes to 30 minutes. In this manner, a surface-crosslinked water absorbent resin (37) and a water absorbing agent (38) were obtained. The physical properties of the surface-crosslinked water absorbent resin (37) and the water absorbing agent (38) thus obtained are shown in Table 4.

Example 13

The same operations as in Example 12 were carried out except that (i) the surface treatment agent mixture solution was changed such that 1,3-propanediol and water were contained (in a mixture ratio (mass ratio) of 1.0:2.6) in an amount of 3.60 parts by mass and (ii) the heating time for a surface crosslinking treatment was changed to 50 minutes. In this manner, a surface-crosslinked water absorbent resin (39) and a water absorbing agent (40) were obtained. The properties of the surface-crosslinked water absorbent resin (39) and the water absorbing agent (40) thus obtained are shown in Table 4.

Comparative Example 11

The same operations as in Example 13 were carried out except that (i) the dew point was changed from 80° C. to 40° C. and (ii) the heat treatment time was changed from 50 minutes to 40 minutes. In this manner, a surface-crosslinked water absorbent resin (37) and a water absorbing agent (38) were obtained. The physical properties of the surface-crosslinked water absorbent resin (37) and the water absorbing agent (38) thus obtained are shown in Table 4.

Reference Example 5

A 500 mL n-heptane was measured out into to a 2-liter four-necked separable flask equipped with a reflux condenser, a dropping funnel, and a nitrogen gas inlet tube. To the flask, 0.92 g of sucrose stearic acid ester (S-370, manufactured by Mitsubishi Foods Corporation) (surfactant) was added. A resultant surfactant was heated to 80° C. and then cooled to 35° C.

Meanwhile, 92.0 g of a 80.5 mass % of acrylic acid aqueous solution was measured out into a 500 mL Erlenmeyer flask. While the Erlenmeyer flask was immersed in an ice bath so as to be cooled from the outside, 153.0 g of a 20.0 mass % of sodium hydroxide aqueous solution was added dropswise to the Erlenmeyer flask for neutralization of the acrylic acid to 75 mol %. Thereafter, the mixture was stirred at room temperature to dissolve completely. To the Erlenmeyer flask, 0.11 g of ammonium persulfate and 0.47 g of polyethyleneglycol diacrylate (molecular weight: 523, the average number (n) of moles of ethylene oxide added is 9) were added, and the mixture was then dissolved so that a first-stage monomer aqueous solution was prepared.

With the stirrer being set to 196 rpm in rotational speed, the monomer aqueous solution was added to the separable flask. The separable flask was held at 35° C. for 30 minutes while the system of the separable flask was replaced with nitrogen. Thereafter, the separable flask was immersed in a hot-water bath of 70° C. for temperature rise so that the polymerization was carried out, thereby obtaining a first-stage post-polymerization slurry.

Meanwhile, 143.2 g of a 80.5 mass % of acrylic acid aqueous solution was measured out into another 500 mL Erlenmeyer flask. While the Erlenmeyer flask was immersed in an ice bath so as to be cooled from the outside, 239.9 g of a 20.0 mass % of sodium hydroxide aqueous solution was added dropswise to the Erlenmeyer flask for neutralization of the acrylic acid to 75 mol %. Thereafter, the mixture was stirred at room temperature to dissolve completely. To the Erlenmeyer flask, 0.11 g of ammonium persulfate and 0.74 g of polyethyleneglycol diacrylate were added, and the mixture was then dissolved so that a second-stage monomer aqueous solution was prepared.

After the number of stirring rotations for the post-polymerization slurry was changed to 480 rpm, the post-polymerization slurry was cooled to a temperature in a range of 26° C. to 30° C. The second-stage monomer aqueous solution was added to the system of the separable flask. The separable flask was held for 30 minutes while being replaced with nitrogen. Thereafter, the separable flask was immersed once again in a hot-water bath of 70° C. for temperature rise so that the polymerization was carried out, thereby obtaining a second-stage post-polymerization slurry.

Subsequently, the separable flask was raised in temperature with use of an oil bath of 120° C., and water and n-heptane were subjected to azeotropy to remove 255.00 g of water out of the system while refluxing n-heptane, after which the separable flask was held at 100° C. for 2 hours. Thereafter, evaporation of n-heptane and drying were carried out to thereby obtain 220 g of a water absorbent resin in the form of second particles which are aggregates of spherical primary particles. The water absorbent resin thus obtained had a middle particle diameter of 400 μm and a moisture content of 6 mass %. The water absorbent resin thus obtained was classified with use of JIS standard sieves having respective mesh sizes of 600 μm and 300 μm for adjustment of particle size distribution. In this manner, a water absorbent resin (5) was obtained. The water absorbent resin (5) thus obtained had CRC of 35.2 g/g, a soluble component of 24.2 wt %, and a mass average particle diameter of 455 μm.

Example 14

The same operations as in Example 13 were carried out except that (i) the water absorbent resin (4) was replaced by the water absorbent resin (5), (ii) the surface treatment agent mixture solution was changed such that 1,4-butanediol, propylene glycol, and water were contained (in a mixture ratio (mass ratio) of 0.3:0.5:2.7) in an amount of 3.50 parts by mass, (iii) the heating temperature was changed to 180° C., and (iv) the heating time for a surface crosslinking treatment was changed to 55 minutes. In this manner, a surface-crosslinked water absorbent resin (39) and a water absorbing agent (40) were obtained. The physical properties of the surface-crosslinked water absorbent resin (39) and the water absorbing agent (40) thus obtained are shown in Table 4.

Comparative Example 12

The same operations as in Example 14 were carried out except that (i) the dew point was changed from 80° C. to 40° C. and (ii) the heat treatment time was changed to 45 minutes. In this manner, a surface-crosslinked water absorbent resin (41) and a water absorbing agent (42) were obtained. The physical properties of the surface-crosslinked water absorbent resin (41) and the water absorbing agent (42) thus obtained are shown in Table 4.

Reference Example 6

In a polymerization container (Dewar bottle) having thermal insulation effectiveness, 155.0 g of acrylic acid, 0.81 g of triallyl isocyanurate aqueous solution (0.15 mol %), and 494.0 g of deionized water were held at 3° C. while being stirred and mixed with each other. After nitrogen was introduced into a resultant mixture so that dissolved oxygen content of the mixture was set to not more than 1 ppm, 15.5 g of a 1 mass % of hydrogen peroxide aqueous solution, 1.9 g of a 2 mass % of ascorbic acid aqueous solution, and 23.2 g of a 2 mass % of 2,2'-azobis[2-methyl-propionamide] dihydrochloride aqueous solution were added and mixed, and polymerization was started. After the temperature of the mixture reached 67° C., polymerization was carried out for about 5 hours at 65° C., thereby obtaining a hydrogel.

Next, 500 g of the hydrogel was mixed with 90.10 g of a 48.5 mass % of sodium hydroxide aqueous solution while being crushed by using a double-arm type stainless kneader having a capacity of 2.5 liters and equipped with two sigma type blades and a jacket, to thereby obtain a crushed gel. Further, the crushed gel was dried for 65 minutes by using a ventilation type band dryer (160° C., air velocity of 2 m/sec) to thereby obtain a water absorbent resin. The water absorbent resin thus obtained was pulverized with use of a roll mill and then classified with use of JIS standard sieves having respective mesh sizes of 850 μm and 150 μm. In this manner, a water absorbent resin (6) was obtained. The water absorbent resin (6) thus obtained had CRC of 34.8 g/g, a soluble component of 8.4 wt %, and a mass average particle diameter of 420 μm.

Example 15

The same operations as in Example 14 were carried out except that (i) the water absorbent resin (5) was replaced by the water absorbent resin (6) and (ii) the heating time for a surface crosslinking treatment was changed to 45 minutes. In this manner, a surface-crosslinked water absorbent resin (39) and a water absorbing agent (40) were obtained. The physical properties of the surface-crosslinked water absorbent resin (39) and the water absorbing agent (40) thus obtained are shown in Table 4. In addition, periods of time required for water absorbent resins to reach predetermined temperatures in the surface crosslinking step are shown in Table 4.

Comparative Example 13

The same operations as in Example 15 were carried out except that (i) the dew point was changed from 80° C. to 40° C. and (ii) the heat treatment time was changed to 35 minutes. In this manner, a surface-crosslinked water absorbent resin (41) and a water absorbing agent (42) were obtained. The physical properties of the surface-crosslinked water absorbent resin (41) and the water absorbing agent (42) thus obtained are shown in Table 4.

Table 1 shown below is a table summarizing atmospheric temperatures, dew points, and heat treatment times, each of which was measured during surface crosslinking in Examples 1 through 11 and in Comparative Examples 1 through 9. Table 3 shown below is a table summarizing (i) atmospheric temperatures, (ii) dew points, (iii) periods of time required for water absorbent resins to reach predetermined temperatures during heating, and (iv) heat treatment times, each of which was measured during surface crosslinking in Examples 12 through 15 and in Comparative Examples 10 through 13.

TABLE 1

|  | Water absorbent resin before surface crosslinking | Atmospheric temperature (° C.) | Atmospheric dew point (° C.) | Heat treatment time (min) | Surface crosslinking water absorbent resin and water absorbing agent |
|---|---|---|---|---|---|
| Example 1 | Water absorbent resin (1) | 197 | 90 | 30 | Surface crosslinking water absorbent resin (1) Water absorbing agent (2) |
| Example 2 | Water absorbent resin (1) | 197 | 70 | 30 | Surface crosslinking water absorbent resin (3) Water absorbing agent (4) |
| Comparative Example 1 | Water absorbent resin (1) | 197 | 40 | 20 | Surface crosslinking water absorbent resin (5) Water absorbing agent (6) |
| Example 3 | Water absorbent resin (1) | 197 | 70 | 20 | Surface crosslinking water absorbent resin (7) Water absorbing agent (8) |
| Comparative Example 2 | Water absorbent resin (1) | 197 | 20 | 20 | Surface crosslinking water absorbent resin (9) Water absorbing agent (10) |
| Example 4 | Water absorbent resin (1) | 197 | 70 | 20 | Surface crosslinking water absorbent resin (11) Water absorbing agent (12) |
| Comparative Example 3 | Water absorbent resin (1) | 197 | 20 | 20 | Surface crosslinking water absorbent resin (13) Water absorbing agent (14) |
| Example 5 | Water absorbent resin (1) | 197 | 70 | 20 | Surface crosslinking water absorbent resin (11) Water absorbing agent (15) |
| Comparative Example 4 | Water absorbent resin (1) | 197 | 40 | 20 | Surface crosslinking water absorbent resin (13) Water absorbing agent (16) |
| Example 6 | Water absorbent resin (2) | 197 | 90 | 40 | Surface crosslinking water absorbent resin (17) Water absorbing agent (18) |
| Comparative Example 5 | Water absorbent resin (2) | 197 | 40 | 30 | Surface crosslinking water absorbent resin (19) Water absorbing agent (20) |
| Comparative Example 6 | Water absorbent resin (2) | 180 | 35 | 30 | Water absorbing agent (21) |
| Example 7 | Water absorbent resin (2) | 180 | 90 | 40 | Water absorbing agent (22) |
| Example 8 | Water absorbent resin (3) | 197 | 90 | 30 | Surface crosslinking water absorbent resin (23) Water absorbing agent (24) |

TABLE 1-continued

|  | Water absorbent resin before surface crossinking | Atmospheric temperature (° C.) | Atmospheric dew point (° C.) | Heat treatment time (min) | Surface crosslinking water absorbent resin and water absorbing agent |
|---|---|---|---|---|---|
| Comparative Example 7 | Water absorbent resin (3) | 197 | 40 | 20 | Surface crosslinking water absorbent resin (25) Water absorbing agent (26) |
| Comparative Example 8 | Water absorbent resin (2) | 180 | 20 | 45 | Water absorbing agent (27) |
| Example 9 | Water absorbent resin (2) | 180 | 80 | 45 | Water absorbing agent (28) |
| Example 10 | Water absorbent resin (2) | 197 | 95 | 45 | Surface crosslinking water absorbent resin (29) Water absorbing agent (30) |
| Example 11 | Water absorbent resin (2) | 197 | 95 | 55 | Surface crosslinking water absorbent resin (31) Water absorbing agent (32) |
| Comparative Example 9 | Water absorbent resin (2) | 197 | 35 | 30 | Surface crosslinking water absorbent resin (33) Water absorbing agent (34) |

TABLE 2

|  | Atmospheric dew point (° C.) | Surface crosslinking water absorbent resin and Water absorbing agent | CRC (g/g) | SFC ($\times 10^{-7}$ cm$^3 \cdot$ sec/g) | AAP (g/g) | PUP (g/g) | Surface soluble component (%) | Extr. (%) | surface-crosslinked strength index |
|---|---|---|---|---|---|---|---|---|---|
| Example 1 | 90 | Surface crosslinking water absorbent resin (1) | 30.0 | 25 | 25.2 | 33.7 |  |  |  |
|  |  | Water absorbing agent (2) | 29.8 | 40 | 24.9 | 33.3 | 1.8 | 11.0 | 16 |
| Example 2 | 70 | Surface crosslinking water absorbent resin (3) | 29.4 | 36 | 25.0 | 33.4 |  |  |  |
|  |  | Water absorbing agent (4) | 29.5 | 58 | 24.4 | 32.6 | 2.5 | 10.5 | 16 |
| Comparative Example 1 | 40 | Surface crosslinking water absorbent resin (5) | 31.0 | 23 | 24.7 | 33.0 |  |  |  |
|  |  | Water absorbing agent (6) | 31.3 | 34 | 23.5 | 31.3 | 6.5 | 11.0 | 59 |
| Example 3 | 70 | Surface crosslinking water absorbent resin (7) | 30.6 | 15 | 24.0 | 32.0 |  |  |  |
|  |  | Water absorbing agent (8) | 30.7 | 28 | 23.6 | 31.5 | 3.5 | 10.9 | 32 |
| Comparative Example 2 | 20 | Surface crosslinking water absorbent resin (9) | 31.3 | 11 | 21.5 | 28.6 |  |  |  |
|  |  | Water absorbing agent (10) | 31.0 | 17 | 20.3 | 26.9 | 7.0 | 11.1 | 63 |
| Example 4 | 70 | Surface crosslinking water absorbent resin (11) | 31.9 | 10 | 23.4 | 31.2 |  |  |  |
|  |  | Water absorbing agent (12) | 31.6 | 13 | 22.6 | 30.1 | 3.0 | 11.6 | 26 |
| Comparative Example 3 | 20 | Surface crosslinking water absorbent resin (13) | 30.5 | 12 | 21.3 | 28.3 |  |  |  |
|  |  | Water absorbing agent (14) | 31.0 | 14 | 19.5 | 25.8 | 5.2 | 11.5 | 45 |
| Example 5 | 70 | Surface crosslinking water absorbent resin (11) | 31.9 | 10 | 23.4 | 31.2 |  |  |  |
|  |  | Water absorbing agent (15) | 32.1 | 16 | 22.8 | 30.4 | 3.0 | 11.4 | 26 |
| Comparative Example 4 | 40 | Surface crosslinking water absorbent resin (13) | 30.5 | 12 | 21.3 | 28.3 |  |  |  |
|  |  | Water absorbing agent (16) | 31.4 | 14 | 20.2 | 26.8 | 5.5 | 11.5 | 48 |
| Example 6 | 90 | Surface crosslinking water absorbent resin (17) | 28.0 | 65 | 23.7 | 31.6 |  |  |  |
|  |  | Water absorbing agent (18) | 27.5 | 110 | 23.5 | 31.3 | 2.1 | 7.4 | 29 |
| Comparative Example 5 | 40 | Surface crosslinking water absorbent resin (19) | 27.5 | 66 | 23.5 | 31.3 |  |  |  |
|  |  | Water absorbing agent (20) | 27.5 | 99 | 22.7 | 30.2 | 5.2 | 7.4 | 71 |
| Comparative Example 6 | 35 | Water absorbing agent (21) | 28.0 | 65 | 23.3 | 31.1 | 6.2 | 7.8 | 79 |
| Example 7 | 90 | Water absorbing agent (22) | 28.5 | 70 | 24.2 | 32.3 | 2.1 | 8.0 | 26 |
| Example 8 | 90 | Surface crosslinking water absorbent resin (23) | 32.6 | 15 | 24.8 | 33.1 |  |  |  |
|  |  | Water absorbing agent (24) | 33.0 | 21 | 24.7 | 33.0 | 1.9 | 15.7 | 12 |
| Comparative Example 7 | 40 | Surface crosslinking water absorbent resin (25) | 34.5 | 4 | 24.3 | 32.4 |  |  |  |
|  |  | Water absorbing agent (26) | 35.1 | 6 | 23.0 | 30.6 | 6.5 | 15.8 | 41 |
| Comparative Example 8 | 20 | Water absorbing agent (27) | 26.1 | 130 | 23.5 | 31.5 | 5.8 | 8.3 | 71 |
| Example 9 | 80 | Water absorbing agent (28) | 26.4 | 125 | 24.3 | 32.4 | 2.5 | 8.3 | 30 |
| Example 10 | 95 | Surface crosslinking water absorbent resin (29) | 28.3 | 33 | 23.8 | — |  |  |  |
|  |  | Water absorbing agent (30) | 27.5 | 101 | 22.1 | — | 1.8 | 6.6 | 27 |

TABLE 2-continued

|  | Atmospheric dew point (° C.) | Surface crosslinking water absorbent resin and Water absorbing agent | CRC (g/g) | SFC (×10⁻⁷ cm³·sec/g) | AAP (g/g) | PUP (g/g) | Surface soluble component (%) | Extr. (%) | surface-crosslinked strength index |
|---|---|---|---|---|---|---|---|---|---|
| Example 11 | 95 | Surface crosslinking water absorbent resin (31) | 27.0 | 54 | 22.6 | — | | | |
|  |  | Water absorbing agent (32) | 26.2 | 163 | 22.3 | — | 1.7 | 6.1 | 28 |
| Comparative Example 9 | 35 | Surface crosslinking water absorbent resin (33) | 27.0 | 67 | 23.1 | — | | | |
|  |  | Water absorbing agent (34) | 26.1 | 99 | 20.7 | — | 4.5 | 8.2 | 55 |

TABLE 3

|  | Water absorbent resin before surface crosslinking | Atmospheric temperature (° C.) | Atmospheric dew point (° C.) | Powder temperature 100° C. Reaching Time (min) | Powder temperature 130° C. Reaching Time (min) | Powder temperature 150° C. Reaching Time (min) | Powder temperature 170° C. Reaching Time (min) | Heat treatment time (min) |
|---|---|---|---|---|---|---|---|---|
| Example 12 | Water absorbent resin (4) | 197 | 80 | 2 | 5 | 10 | 15 | 40 |
| Comparative Example 10 | Water absorbent resin (4) | 197 | 40 | 2 | 4 | 9 | 14 | 30 |
| Example 13 | Water absorbent resin (4) | 197 | 80 | 2 | 5 | 10 | 15 | 50 |
| Comparative Example 11 | Water absorbent resin (4) | 197 | 40 | 2 | 4 | 9 | 14 | 40 |
| Example 14 | Water absorbent resin (5) | 180 | 80 | 3 | 12 | 18 | 25 | 55 |
| Comparative Example 12 | Water absorbent resin (5) | 180 | 40 | 3 | 10 | 15 | 23 | 45 |
| Example 15 | Water absorbent resin (6) | 197 | 80 | 2 | 5 | 10 | 15 | 45 |
| Comparative Example 13 | Water absorbent resin (6) | 197 | 40 | 2 | 4 | 9 | 14 | 35 |

TABLE 4

|  | Atmospheric dew point (° C.) | Surface crosslinking water absorbent resin and Water absorbing agent | CRC (g/g) | SFC (×10⁻⁷ cm³·sec/g) | AAP (g/g) | PUP (g/g) | Surface soluble component (%) | Extr. (%) | surface-crosslinked strength index |
|---|---|---|---|---|---|---|---|---|---|
| Example 12 | 80 | Surface crosslinking water absorbent resin (35) | 27.1 | (×10⁻⁷ cm³·sec/g) | 25.0 | — | | | |
|  |  | Water absorbing agent (36) | 27.0 |  | 24.6 | — | 2 | 6.9 | 29 |
| Comparative Example 10 | 40 | Surface crosslinking water absorbent resin (37) | 27.3 | 92 | 23.1 | — | | | |
|  |  | Water absorbing agent (38) | 27.4 | 99 | 21.5 | — | 4.5 | 7.9 | 57 |
| Example 13 | 80 | Surface crosslinking water absorbent resin (39) | 27.3 | 118 | 24.7 | — | | | |
|  |  | Water absorbing agent (40) | 27.2 | 164 | 24.5 | — | 2.3 | 6.5 | 35 |
| Comparative Example 11 | 40 | Surface crosslinking water absorbent resin (41) | 27.2 | 90 | 23.1 | — | | | |
|  |  | Water absorbing agent (42) | 27.4 | 100 | 21.2 | — | 4.5 | 7.4 | 61 |
| Example 14 | 80 | Surface crosslinking water absorbent resin (43) | 28.1 | 115 | 23.4 | — | | | |
|  |  | Water absorbing agent (44) | 28.3 | 140 | 22.9 | — | 9 | 23.2 | 39 |
| Comparative Example 12 | 40 | Surface crosslinking water absorbent resin (45) | 27.9 | 70 | 21.5 | — | | | |
|  |  | Water absorbing agent (46) | 27.8 | 85 | 20.0 | — | 18 | 24.2 | 74 |
| Example 15 | 80 | Surface crosslinking water absorbent resin (47) | 29.3 | 5 | 22.5 | — | | | |
|  |  | Water absorbing agent (48) | 29.1 | 15 | 22.0 | — | 2.9 | 8.5 | 34 |
| Comparative Example 13 | 40 | Surface crosslinking water absorbent resin (49) | 29.1 | 4 | 21.5 | — | | | |
|  |  | Water absorbing agent (50) | 29.0 | 11 | 20.2 | — | 4.7 | 8.2 | 57 |

(Summary)

Comparisons on Table 2 between (a) Examples 1 and 2 and (b) Comparative Example 1, between Example 3 and Comparative Example 2, between Example 4 and Comparative Example 3, between Example 5 and Comparative Example 4, between Example 6 and Comparative Example 5, between Example 8 and Comparative Example 7, and between (a) Examples 10 and 11 and (b) Comparative Example 9, and comparisons on Table 4 between Example 12 and Comparative Example 10, between Example 13 and Comparative Example 11, between Example 14 and Comparative Example 12, and between Example 15 and Comparative Example 13 show that in a case where a heat treatment is carried out at a dew point of not less than 45° C., (i) the amount of decrease in absorption capacity under load as a result of addition of a liquid permeability enhancer is smaller than that in a case where a heat treatment is carried out at a dew point of less than 45° C. and (ii) a value of the absorption capacity under load is high.

The amounts of increase in liquid permeability as a result of addition of a liquid permeability enhancer shown in Examples 10 and 11 are significantly larger than that shown in Comparative Example 9. A comparison of Example 7 with Comparative Example 6 and a comparison of Example 9 with Comparative Example 8 indicate that, in Example 7 and in Example 9, strong surface-crosslinked layers were formed so as to restrict a decrease in absorption capacity which occurs as a result of addition of liquid permeability enhancers. This is because the respective values of absorption capacity under load in Example 7 and in Example 9 are high, although liquid permeability enhancers and surface crosslinking agent solutions were simultaneously added and therefore the amounts of decrease in absorption capacity under load which occurs as a result of the addition of the liquid permeability enhancers are unclear.

In the case where a heat treatment was carried out at a dew point of not less than 45° C., a water absorbing agent showed such physical properties as a surface soluble component of not more than 4 mass % and a surface-crosslinked layer strength index of not more than 40. These two physical properties thus show (i) the amount of decrease in absorption capacity under load that occurs as a result of addition of a liquid permeability enhancer is small and (ii) the value of the absorption capacity under load is high. This indicates such an advantageous effect of the water absorbing agent of the present invention as producing a strong surface-crosslinked layer.

The present invention is not limited to the description of the embodiments, but can be altered in many ways by a person skilled in the art within the scope of the claims. An embodiment derived from a proper combination of technical means disclosed in different embodiments is also encompassed in the technical scope of the present invention. Furthermore, new technical features can be obtained by the combination of the technical means disclosed in different embodiments.

(Summary of the Present Invention)

The present invention is a method for producing a polyacrylic acid (salt)-based water absorbing agent, comprising: a surface crosslinking agent addition step of adding a surface crosslinking agent solution; a liquid permeability enhancer addition step of adding a liquid permeability enhancer, the liquid permeability enhancer addition step being performed simultaneously with and/or after the surface crosslinking agent addition step; and a surface crosslinking step of carrying out a heat treatment in conditions in which an atmospheric dew point is at least in a range of 45° C. to 100° C., the surface crosslinking step being performed simultaneously with or after the surface crosslinking agent addition step.

The method is preferably configured such that during the heat treatment in the surface crosslinking step, an upper limit of a temperature of a water absorbent resin powder is 175° C. to 300° C.

The method is preferably configured such that the atmospheric dew point is in the range of 45° C. to 100° C. during a period of time which is not less than 10% of an entire period of the heat treatment time in the surface crosslinking step.

The method is more preferably configured such that the atmospheric dew point is controlled to be in the range of 45° C. to 100° C. at a point in time where the temperature of the water absorbent resin powder reaches not less than 100° C. in the surface crosslinking step.

The method is preferably configured such that: the liquid permeability enhancer is at least one substance selected from a water-soluble polyvalent metal cation-containing compound, water-insoluble inorganic fine particles, and a cationic polymer compound; and an amount of the liquid permeability enhancer added is in a range of 0.01 parts by mass to 5 parts by mass, relative to 100 parts by mass of the water absorbent resin powder.

The method is preferably configured such that the surface crosslinking agent solution contains an organic surface crosslinking agent that forms, by a heat treatment, a covalent bond with a carboxyl group existing on the periphery of a surface of a water absorbent resin.

The method is preferably configured such that the surface crosslinking agent solution contains (i) at least one compound selected from a polyhydric alcohol compound, amino alcohol, alkylene carbonate, an oxazolidinone compound, and an epoxy compound, each of which is an organic surface crosslinking agent. The surface crosslinking agent solution particularly preferably contains (i) an alkylene carbonate compound or (ii) an alkylene carbonate compound and at least one compound selected from the above organic surface crosslinking agents other than the alkylene carbonate compound.

An amount of the organic surface crosslinking agent added is preferably in a range of 0.01 parts by mass to 10 parts by mass relative to 100 parts by mass of the water absorbent resin powder. Furthermore, the organic surface crosslinking agent can contain water, an amount of the water being preferably in a range of 0 part by mass to 10 parts by mass relative to 100 parts by mass of the water absorbent resin powder.

The method is preferably configured such that the temperature of the polyacrylic acid (salt)-based water absorbent resin powder provided in the surface crosslinking agent addition step is in a range of 30° C. to 100° C. It is not preferable that the temperature is less than 30° C. because, in such a case, there is a risk of causing difficulty in handling of the water absorbent resin during production, such as a case where the water absorbent resin absorbs moisture and therefore causes fluidity to decrease. It is also not preferable that the temperature exceeds 100° C. because, in such a case, rapid evaporation or absorption of the surface crosslinking agent solution and/or partial reaction may be induced, thereby preventing the surface crosslinking agent from being uniformly added. Furthermore, a temperature of a mixture of the organic surface crosslinking agent and the polyacrylic acid (salt)-based water absorbent resin powder is preferably in a range of 30° C. to 100° C.

The method is preferably configured such that a length of time for which the heat treatment in the surface crosslinking step lasts is in a range of 1 minute to 120 minutes.

The heat treatment in the surface crosslinking step only needs to be carried out such that the maximum temperature of the water absorbent resin powder, which is an object to be heated in the surface crosslinking step, is higher than an atmospheric dew point, and is preferably in a range of 175° C. to 300° C. It is not preferable that the temperature is less than 175° C. because, in such a case, formation of a covalent bond for surface crosslinking may be insufficient. It is also not preferable that the temperature exceeds 300° C. because, in such a case, the water absorbent resin may deteriorate.

The period of time for which the heat treatment lasts only needs to satisfy conditions required for the temperature above, and is normally in a range of 1 minute to 120 minutes.

It is preferable to perform a disintegration step and/or a classification step after the surface crosslinking step so as to obtain a water absorbing agent having a particle diameter of less than 1 mm (the particle diameter is herein defined by sieve classification unless specified otherwise). A less amount of particles having a particle diameter of not less than 850 μm is preferable. Such particles in amount relative to the water absorbing agent is preferably less than 5 mass %, more preferably not more than 3 mass %, and still more preferably not more than 1 mass %.

A less amount of fine particles having a particle diameter of less than 150 μm is preferable. Such particles in amount is preferably less than 5 mass %, more preferably not more than 3 mass %, and still more preferably not more than 1.5 mass %. The water absorbing agent preferably contains particles having a particle diameter of less than 300 am. The amount of such particles is more preferably not less than 10 mass %, and is preferably not more than 50 mass %, and more preferably not more than 30 mass %. The amount of particles having a particle diameter of 150 μm to 850 μm contained in the water absorbent resin is preferably not less than 95 mass %, more preferably not less than 98 mass %, and still more preferably not less than 99 mass %.

A mass average particle diameter of the water absorbent resin is preferably not less than 200 μm and not more than 600 μm, more preferably in the range of 200 μm to 550 μm, still more preferably in the range of 250 μm to 500 μm, and most preferably in the range of 350 μm to 450 μm.

A second one of the present invention is polyacrylic acid (salt)-based water absorbing agent having a surface, a periphery of which surface is cross-linked by an organic surface crosslinking agent and is provided with a liquid permeability enhancer, the polyacrylic acid (salt)-based water absorbing agent satisfying the following requirements (A) through (D):
(A) CRC is 25 g/g to 35 g/g;
(B) SFC is not less than $10(\times 10^{-7} \text{ cm}^3 \cdot \text{sec/g})$;
(C) soluble component is 5 mass % to 20 mass %; and
(D) surface-crosslinked layer strength index is not more than 40 (provided that surface-crosslinked layer strength index is defined by the following equation: surface-crosslinked layer strength index-surface soluble component (%)/soluble component (%)×100).

SFC is not less than $10(\times 10^{-7} \text{ cm}^3 \cdot \text{sec/g})$, more preferably not less than $15(\times 10^{-7} \text{ cm} \cdot \text{sec/g})$, and still more preferably not less than $20(\times 10^{-7} \text{ cm}^3 \cdot \text{sec/g})$, not less than $30(\times 10^{-7} \text{ cm}^3 \cdot \text{sec/g})$, not less than $50(\times 10^{-7} \text{ cm}^3 \cdot \text{sec/g})$, and not less than $70(\times 10^{-7} \text{ cm}^3 \cdot \text{sec/g})$.

The soluble component needs to be in a range of 5 mass % to 20 mass %, and is preferably in a range of 5 mass % to 18 mass %, and more preferably in a range of 5 mass % to 15 mass %.

The surface-crosslinked layer strength index needs to be not more than 40, preferably not more than 35, more preferably not more than 30, and particularly preferably not more than 25. For the sake of calculation, a lower limit is not less than 0.

The 0.58 psi PUP of the water absorbing agent is preferably not less than 30 (g/g), more preferably not less than 31 (g/g), and still more preferably not less than 32 (g/g).

The surface soluble component of the water absorbing agent is preferably in a range of 0 mass % to 4.5 mass %, more preferably in a range of 0 mass % to 3.5 mass %, and still more preferably in a range of 0 mass % to 3.0 mass %.

The water absorbing agent is preferably configured such that the liquid permeability enhancer is a cationic polymer compound.

INDUSTRIAL APPLICABILITY

The production method of the present invention makes it possible to obtain, with high productivity and with a low amount of residual surface crosslinking agent, a water absorbing agent having excellent physical properties (especially high liquid permeability and Anti-Caking property). This allows a large amount of inexpensive and highly safe water absorbing agents to be supplied for sanitary materials such as disposable diapers.

The invention claimed is:
1. A method for producing a polyacrylic acid (salt)-based water absorbing agent, comprising:
   a surface crosslinking agent addition step of adding a surface crosslinking agent solution to a polyacrylic acid (salt)-based water absorbent resin powder;
   a liquid permeability enhancer addition step of adding a liquid permeability enhancer, the liquid permeability enhancer addition step being performed simultaneously with and/or after the surface crosslinking agent addition step; and
   a surface crosslinking step of carrying out a heat treatment in conditions in which an atmospheric dew point is in a range of 45° C. to 100° C., the surface crosslinking step being performed simultaneously with or after the surface crosslinking agent addition step, wherein the heating apparatus for use in the heat treatment is a continuous type or batch type heating apparatus including a gas discharge mechanism and/or a gas supply mechanism, and a flow rate of an airflow supplied to and/or discharged from the heating apparatus is more than 0 Nm³ but not more than 10,000 Nm³/hr, or a ratio of gas relative to the amount of the polyacrylic acid (salt)-based water absorbent resin powder to be processed is not more than 3,000 Nm³/ton,
   wherein the liquid permeability enhancer addition step performed simultaneously with the surface crosslinking agent addition step means that (i) the liquid permeability enhancer is mixed into the surface crosslinking agent or into the surface crosslinking agent solution to obtain a mixture and then adding the mixture, (ii) the liquid permeability enhancer is added simultaneously with the surface crosslinking agent or with the surface crosslinking agent solution without being mixed with the surface crosslinking agent or with the surface crosslinking agent solution, or (iii) the liquid permeability enhancer is added at a stage previous to the surface crosslinking agent addition step, and
   obtaining the polyacrylic acid (salt)-based water absorbing agent.
2. The method as set forth in claim 1, wherein
   during the heat treatment in the surface crosslinking step, an upper limit of a temperature of the water absorbent resin powder is 175° C. to 300° C.

3. The method as set forth in claim 1, wherein
the atmospheric dew point is in the range of 45° C. to 100° C. during a period of time which is not less than 10% of an entire period of the heat treatment in the surface crosslinking step.

4. The method as set forth in claim 1, wherein
the atmospheric dew point is in the range of 45° C. to 100° C. at a point when the temperature of the water absorbent resin powder reaches not less than 100° C. in the surface crosslinking step.

5. The method as set forth in claim 1, wherein
the liquid permeability enhancer is at least one substance selected from the group consisting of a water-soluble polyvalent metal cation-containing compound, water-insoluble inorganic fine particles, and a cationic polymer compound.

6. The method as set forth in claim 1, wherein
the amount of the liquid permeability enhancer added is in a range of 0.01 parts by mass to 5 parts by mass relative to 100 parts by mass of the water absorbent resin powder.

7. The method as set forth in claim 1, wherein
the surface crosslinking agent solution contains (i) at least one compound selected from the group consisting of a polyhydric alcohol compound, amino alcohol, alkylene carbonate, an oxazolidinone compound, and an epoxy compound, each of which is an organic surface crosslinking agent.

8. The method as set forth in claim 7, wherein
the amount of the organic surface crosslinking agent contained in the surface crosslinking agent solution is in a range of 0.1 parts by mass to 10 parts by mass relative to 100 parts by mass of the water absorbent resin powder.

9. The method as set forth in claim 1, wherein
the surface crosslinking agent solution contains water, the amount of the water being in a range of 1 part by mass to 10 parts by mass relative to 100 parts by mass of the water absorbent resin powder.

10. The method as set forth in claim 1, wherein
the temperature of the water absorbent resin powder in the surface crosslinking agent addition step is in a range of 30° C. to 100° C.

11. The method as set forth in claim 1, wherein
a length of time of the heat treatment in the surface crosslinking step is in a range of 1 minute to 120 minutes.

12. The method of claim 1, wherein said gas discharge mechanism and/or gas supply mechanism controls the atmospheric dew point and temperature during the surface crosslinking step.

* * * * *